(12) United States Patent
Babish et al.

(10) Patent No.: US 8,535,740 B2
(45) Date of Patent: Sep. 17, 2013

(54) **COMPOSITIONS FROM *NIGELLA SATIVA***

(75) Inventors: John George Babish, Ithaca, NY (US); Linda M. Pacioretty, Brooktondale, NY (US); Jan Debenedetto, Towaco, NJ (US)

(73) Assignee: Bionexus, Ltd., Ithaca, NY (US)

( * ) Notice: Subject to any disclaimer, the term of this patent is extended or adjusted under 35 U.S.C. 154(b) by 214 days.

(21) Appl. No.: 12/927,873

(22) Filed: Nov. 29, 2010

(65) Prior Publication Data

US 2011/0076346 A1 Mar. 31, 2011

Related U.S. Application Data

(63) Continuation-in-part of application No. 12/220,811, filed on Jul. 29, 2008, now Pat. No. 8,029,831, and a continuation-in-part of application No. 11/821,221, filed on Jun. 22, 2007, now Pat. No. 8,093,292, which is a continuation-in-part of application No. 10/699,195, filed on Oct. 31, 2003, now Pat. No. 8,017,651.

(60) Provisional application No. 60/428,246, filed on Nov. 22, 2002, provisional application No. 61/283,490, filed on Dec. 4, 2009.

(51) Int. Cl.
*A61K 36/00* (2006.01)

(52) U.S. Cl.
USPC .......................................... 424/776; 424/725

(58) Field of Classification Search
None
See application file for complete search history.

(56) References Cited

U.S. PATENT DOCUMENTS

| 6,231,866 | B1 * | 5/2001 | Mann | 424/732 |
| 2002/0168429 | A1 * | 11/2002 | Mann | 424/732 |
| 2007/0243310 | A1 * | 10/2007 | Leonard et al. | 426/651 |
| 2008/0299234 | A1 * | 12/2008 | Schrezenmeir | 424/745 |

OTHER PUBLICATIONS

Machmudah et al. Separation Sci. Technol. 2005. vol. 40, pp. 1267-1275.*
Fullana et al. Chem. Engineerring Sci. 1999. vol. 54, pp. 5845-5862.*
El-Ghorab, A. J. Essential Oil-Bearing Plants. 2003. vol. 6, No. 2, pp. 67-77.*
Wawryzniak et al. Inzynieria i Aparatura Chemiczna. 2004. vol. 43 (3, Spec. Issue), pp. 161-162.*
Alhaj et al. Am. J. Pharmacol. Toxicol. 2008. vol. 3, No. 4, pp. 225-228.*

* cited by examiner

*Primary Examiner* — Chris R Tate

(57) ABSTRACT

Described are four, novel supercritical fluid extracts of *Nigella sativa* seeds containing about 0.01 to about 40% (w/w) thymoquinone that can be produced using commercial-scale quantities of *N. sativa* seeds. These formulations provide antioxidant, thermogenic, anti-inflammatory and other biological activities qualitatively and quantitatively distinct from thymoquinone alone and are useful as dietary supplements or therapeutics for inflammation-related disorders.

3 Claims, 12 Drawing Sheets

[A]

[B]

COMPOSITIONS FROM *NIGELLA SATIVA*

CROSS-REFERENCE TO RELATED APPLICATIONS

This patent application claims priority to U.S. provisional application Ser. No. 61/283,490 filed on Dec. 4, 2009. This application is a continuation-in-part of U.S. application Ser. No. 12/220,811 filed Jul. 29, 2008 now U.S. Pat. No. 8,029,831. This application is also a continuation-in-part of U.S. application Ser. No. 11/821,221 filed Jun. 22, 2007, now U.S. Pat. No. 8,093,292 which is a continuation-in-part of U.S. application Ser. No. 10/699,195 filed Oct. 31, 2003, now U.S. Pat. No. 8,017,651 which claims the benefit under 35 U.S.C. §119(e) to provisional application No. 60/428,246, filed Nov. 22, 2002, the entirety of which are incorporated herein by reference.

BACKGROUND OF THE INVENTION

1. Field of the Invention

The present invention relates to four novel compositions of *Nigella sativa* that function uniquely to reduce oxidative stress, inhibit secretion of prostate specific antigen (PSA) from prostate cells, uncouple mitochondrial membrane potential, inhibit inducible nitric oxide synthase (iNOS) in inflamed fat and muscle tissue, modify fatty acid flux, activate myocyte AMP-activated protein Kinase (AMPK), and inhibit loss of transepithelial electrical resistance (TEER) in stressed intestinal epithelial cells in a manner that is unexpectedly both quantitatively and qualitatively superior to thymoquinone (TQ), the putative active phytochemical of *N. sativa* (FIG. 1). These compositions would be useful in the prevention or treatment of metabolic disorders such as adaptive thermogenesis, obesity, diabetes, and metabolic syndrome as well as hyperlipidemia, hypertension and exercise recovery. The compositions would also be useful in the treatment or amelioration of benign prostate hyperplasia.

2. Description of the Related Art

*Nigella sativa*, commonly known as black seed or black curcumin, is traditionally used in the Indian subcontinent, Arabian countries, and Europe for culinary and medicinal purposes as a natural remedy for a number of illnesses and conditions that include asthma, hypertension, diabetes, inflammation, cough, bronchitis, headache, eczema, fever, dizziness and influenza. Much of the biological activity of the seeds is believed to be due to TQ, a component of the essential oil, which is also present in the fixed oil.

The seeds of *N. sativa* as well as TQ are characterized by a very low degree of toxicity. Administration of either the seed, its extract or its oil has been shown not to induce significant toxicity or adverse effects on liver or kidney functions even at extremely high doses [Ali B H, Blunden G. 2003. Pharmacological and toxicological properties of *Nigella sativa*. *Phytother Res* 17: 299-305]. Thus, *N. sativa* seed and TQ possess the necessary safety factor for commercialization in the dietary supplement or pharmaceutical market.

TABLE 1

Chemical Content of Various Oil Fractions of *N sativa* Seeds

| SEED FRACTION | COMPONENT | CONTENT [% [w/w] |
|---|---|---|
| Fixed Oils | | 36 |
| Non-fat components | Fatty acids, protein, thiamin, ribovflavin, pyridoxine, niacin, folic acid, and calcium. | 58 |
| Essential fatty acids in fixed oil | Myristic acid (C14) | 0.5 |
| | Palmitic acid (C16) | 13.7 |
| | Palmitoleic acid (C16 ω-9) | 0.1 |
| | Stearic acid (C18) | 2.6 |
| | Linoleic acid (C18 ω-6) | 57.9 |
| | Linolenic acid (C18 ω-3) | 0.2 |
| | Arachidic acid (C20) | 1.3 |

Essential oil components (0.5-1.5%): α-Pinene, camphene, β-pinene, sabinene, β-myrcene, α-terpinene, limonene, β-phellandrene, 1,8-cineole, γ-terpinene, p-cymene (7.1-15.5%), α-terpinolene, 2-heptanal, thujone, trans-sabinenehydrate, longipinene, camphor, linalool, cis-Sabinenehydrate, longifoline (1.0-8.0%), bornylacetate, 2-undecanone, 4-terpineol (2.0-6.6%), borneol, carvone, thymoquinone (27-57%), 2-tridecanone, t-anethole (0.25-2.3%), p-cymene-8-ol, p-anisaldehyde, thymol and carvacrol (5.8-11.6%) (Bunts, M.; Bucar, F., Antioxidant activity of *Nigella sativa* essential oil. Phytother Res 2000,14 (5), 323-8).

As seen in Table 1, the TQ or dithymoquinone content of the essential (volatile) oil fraction is roughly 27-57 percent. The essential oil fraction, however, constitutes only one percent of the seed oils. Thus, TQ comprises only about 0.3 to 0.6% of the fixed oil fraction, the most common commercially available product of *N. sativa* seeds.

Extraction processes—Traditional solvent extraction is time-consuming, requires multiple steps, and consumes large amounts of organic solvents. The amount and the price of organic solvent directly influences the total cost of producing an acceptable extract or product. Moreover, when the final product is used as a food ingredient, it is absolutely necessary to remove all potentially toxic solvents.

Supercritical fluid extraction (SFE) has already proven itself as an attractive technique for selectively removing compounds from complex food matrices. Extraction with liquid or supercritical $CO_2$ is essentially a simple concept, although specialized equipment and technically skilled operators are needed to bring concept to reality. $CO_2$ can exist in solid, liquid or gaseous phase, in common with all chemical substances. Furthermore, if the liquid phase is taken beyond the so-called critical points of temperature and pressure, a supercritical fluid is formed, which in simple terms can be considered as a dense gas 1. Both liquid and supercritical $CO_2$ act effectively as solvents. While liquid $CO_2$ is excellent for dissolving relatively non-polar, small molecules (liquid $CO_2$ can be compared to hexane in this regard), supercritical $CO_2$ allows the extraction of larger and more polar compounds. Thus, supercritical extraction has the potential for creating novel extracts of commonly used herbs.

Supercritical $CO_2$ is pumped through the plant material in the extraction columns, where extraction of the desired plant components takes place. After passing through the expansion valve, the extract-laden $CO_2$ is depressurised and the extract precipitates out of solution in the separator. The gaseous $CO_2$ can be recycled for further extractions (FIG. 2).

What sets liquid and supercritical $CO_2$ apart from other solvents such as hexane and ethanol are two key properties. Firstly, once the extraction has been effected, the $CO_2$ solvent is released as a gas and recycled in the process, so that a solvent-free extract is produce. This has two immediate benefits—the extract is free of all solvent residues, and importantly so is the extracted material, which can then be further used for processing if required. Secondly, the solvating power of $CO_2$ can be manipulated readily by altering temperature and pressure. This means that extraction can be highly selective and novel.

Obesity is a disease resulting from a prolonged positive imbalance between energy intake and energy expenditure. In 2000, an estimated 30.5% of adults in the U.S. were obese (i.e. had a body mass index [BMI] greater than 30 kg/m$^2$) and 15.5% of adolescents were overweight (BMI of 25 to 30 kg/m$^2$). Excess body weight is one of the most important risk factors for all-cause morbidity and mortality. The likelihood of developing conditions such as type 2 diabetes, heart disease, cancer and osteoporosis of weight-bearing joints increases with body weight. The rapidly increasing worldwide incidence of obesity and its association with serious comorbid diseases means it is beginning to replace undernutrition and infectious diseases as the most significant contributor to ill health in the developed world.

It is now generally accepted that adipose tissue acts as an endocrine organ producing a number of biologically active peptides with an important role in the regulation of food intake, energy expenditure and a series of metabolic processes. Adipose tissue secretes a number of bioactive peptides collectively termed adipokines. Through their secretory function, adipocytes lie at the heart of a complex network capable of influencing several physiological processes. Dysregulation of adipokine production with alteration of adipocyte mass has been implicated in metabolic and cardiovascular complications of obesity. In obese individuals, excessive production of acylation-stimulating protein (ASP), TNFα, IL-6 or resistin deteriorates insulin action in muscles and liver, while increased angiotensinogen and PAI-1 secretion favors hypertension and impaired fibrinolysis. Leptin regulates energy balance and exerts an insulin-sensitizing effect. These beneficial effects are reduced in obesity due to leptin resistance. Adiponectin increases insulin action in muscles and liver and exerts an anti-atherogenic effect. Further, adiponectin is the only known adipokine whose circulating levels are decreased in the obese state. The thiazolidinedione anti-diabetic drugs increase plasma adiponectin, supporting the idea that adipokine-targeted pharmacology represents a promising therapeutic approach to control type 2 diabetes and cardiovascular diseases in obesity.

Metabolism of white adipose tissue is involved in the control of body fat content, especially visceral adipose tissue. Adipose tissue plays a central role in the control of energy homeostasis through the storage and turnover of triglycerides and through the secretion of factors that affect satiety and fuel utilization. Mitochondrial remodeling and increased energy expenditure in white fat may affect whole-body energy homeostasis and insulin sensitivity [Wilson-Fritch L, Nicoloro S, Chouinard M, Lazar M A, Chui P C, et al. 2004. Mitochondrial remodeling in adipose tissue associated with obesity and treatment with rosiglitazone. *J Clin Invest* 114: 1281-9].

Oxidative stress—Current consensus is that hyperglycemia results in the production of reactive oxygen (oxidative stress) and nitrogen species, which leads to oxidative myocardial injury. Alterations in myocardial structure and function occur in the late stage of diabetes. These chronic alterations are believed to result from acute cardiac responses to suddenly increased glucose levels at the early stage of diabetes. Oxidative stress, induced by reactive oxygen and nitrogen species derived from hyperglycemia, causes abnormal gene expression, altered signal transduction, and the activation of pathways leading to programmed myocardial cell deaths. The resulting myocardial cell loss thus plays a critical role in the development of diabetic cardiomyopathy.

Mitochondrial uncoupling—Controlling adiposity by targeted modulation of adipocyte mitochondrial membrane potential could offer an attractive alternative to current dietary approaches. It has recently been reported that forced uncoupling protein 1 (UCP1) expression in white adipocytes derived from a murine (3T3-L1) preadipocyte cell line reduced the total lipid accumulation by approximately 30% without affecting other adipocyte markers, such as cytosolic glycerol-3-phosphate dehydrogenase activity and leptin production. The expression of UCP1 also decreased glycerol output and increased glucose uptake, lactate output, and the sensitivity of cellular ATP content to nutrient removal [Si Y, Palani S, Jayaraman A, Lee K. 2007. Effects of forced uncoupling protein 1 expression in 3T3-L1 cells on mitochondrial function and lipid metabolism. *J Lipid Res* 48: 826-36]. These results suggest that the targeting reduction in intracellular lipid of adipocytes by uncoupling mitochondrial membrane potential represents a feasible mechanism for identification of anti-obesity molecules. Nevertheless, the putative role of various mitochondrial protonophores in white fat cells in the control of adiposity remains to be clarified.

Thermogenesis—Thermogenesis or uncoupling of mitochondrial membrane potential may be activated both indirectly and directly. Indirect activation occurs through β3AR and β3 agonists (β3AA). In the early 1980s, an "atypical" beta-adrenergic receptor was discovered and subsequently called β3AR. Further clinical testing will be necessary, using compounds with improved oral bioavailability and potency, to help assess the physiology of the β3AR in humans and its attractiveness as a potential therapeutic for the treatment of type 2 diabetes and obesity [de Souza C J, Burkey B F. 2001. Beta 3-adrenoceptor agonists as anti-diabetic and anti-obesity drugs in humans. *Curr Pharm Des* 7: 1433-49].

Adaptive thermogenesis—Adaptive thermogenesis represents the decrease in energy expenditure (EE) beyond what could be predicted from the changes in fat mass or fat-free mass under conditions of standardized physical activity in response to a decrease in energy intake. Thus there exists the potential of adaptive thermogenesis to impede obesity treatment on a short- and long-term basis, at least in some individuals. In some cases, the adaptive decrease in thermogenesis was shown to be significantly related to a single cycle of body weight loss and regain, an increase in plasma organochlorine concentration following weight loss. This suggests that energy metabolism might be sensitive to stimuli of different physiological nature and that adaptive thermogenesis could be quantitatively more important than what is generally perceived by health professionals and nutrition specialists. However, from a clinical point of view, several issues remain to be investigated in order to more clearly identify adaptive thermogenesis determining factors and to develop strategies to cope with them. Along these lines, it is concluded that unsuccessful weight loss interventions and reduced body weight maintenance could be partly due, in some vulnerable individuals, to the adaptive thermogenesis, which is multicausal, quantitatively significant, and has the capacity to compensate for a given prescribed energy deficit, possibly going beyond any good compliance of some patients.

Additional approaches to increasing thermogenesis appear necessary to affect sustained weight loss in obese subjects. One of these approaches with demonstrated proof-of-concept in humans is direct, chemical stimulation of thermogenesis through chemical uncoupling of mitochondrial membrane potential using 2,4-dinitrophenol (DNP). Doubling metabolic rate by selectively and modestly uncoupling adipocyte thermogenesis should produce few adverse side-effects as this level of increase would only be equivalent to mild exercise. DNP is a lipid—soluble, weak acid that acts as a protonophore because it can cross membranes protonated, lose its proton and return as the anion, then reprotonate and repeat the cycle. In this way, it increases the basal proton conductance of mitochondria and uncouples oxidative phosphorylation. The overall result is a decrease in ATP formation for an equivalent amount of oxidation.

Inducible nitric oxide synthase—Obesity leading to insulin resistance is a major causative factor for type 2 diabetes and is associated with increased risk of cardiovascular disease. Despite intense investigation for a number of years, molecular mechanisms underlying insulin resistance remain to be determined. Recently, chronic inflammation has been highlighted as a culprit for obesity-induced insulin resistance. Nonetheless, upstream regulators and downstream effectors of chronic inflammation in insulin resistance remain unclarified. Inducible nitric oxide synthase (iNOS), a mediator of inflammation, has emerged as an important player in insulin resistance. Obesity is associated with increased iNOS expression in insulin-sensitive tissues in rodents and humans. Inhibition of iNOS ameliorates obesity-induced insulin resistance. However, molecular mechanisms by which iNOS mediates insulin resistance via nitric oxide (NO) biosynthesis remain largely unknown.

NO is a critically important signaling molecule, controlling a wide range of pathways and biological processes. Highly reactive nitric oxide mediates its function through reaction with different molecules directly or indirectly. One of these modifications is the S-nitrosylation of cysteine residues in proteins. S-nitrosylation is emerging as an important redox signaling mechanism and has been found to regulate a broad range of biologic, physiologic and cellular functions [Hausladen, A., and Stamler, J. S. Nitrosative stress. *Methods Enzymol* 1999, 300, 389-95].

Protein S-nitrosylation, a covalent attachment of NO moiety to thiol sulfhydryls, has emerged as a major mediator of a broad array of NO actions. S-nitrosylation is elevated in patients with type 2 diabetes, and increased S-nitrosylation of insulin signaling molecules, including insulin receptor, insulin receptor substrate-1, and Akt/PKB, has been shown in skeletal muscle of obese, diabetic mice. Akt/PKB is reversibly inactivated by S-nitrosylation. Based on these findings, S-nitrosylation has recently been proposed to play an important role in the pathogenesis of insulin resistance [Kaneki, M., Shimizu, N., Yamada, D., and Chang, K. Nitrosative stress and pathogenesis of insulin resistance. *Antioxid Redox Signal* 2007, 9, 319-29].

Moreover iNOS expression is increased in skeletal muscle of diabetic (ob/ob) mice compared with lean wild-type mice. iNOS gene disruption or treatment with iNOS inhibitor ameliorates depressed IRS-1 expression in skeletal muscle of diabetic (ob/ob) mice. These findings indicate that iNOS reduces IRS-1 expression in skeletal muscle via proteasome-mediated degradation and thereby may contribute to obesity-related insulin resistance[Sugita, H., Fujimoto, M., Yasukawa, T., Shimizu, N., Sugita, M., Yasuhara, S., Martyn, J. A., and Kaneki, M. Inducible nitric-oxide synthase and NO donor induce insulin receptor substrate-1 degradation in skeletal muscle cells. *J Biol Chem* 2005, 280, 14203-11].

Improvements in the treatment of noncardiac complications from diabetes have resulted in heart disease becoming a leading cause of death in diabetic patients. Pathogenesis of diabetic cardiomyopathy (DCM) is a complicated and chronic process that is secondary to acute cardiac responses to diabetes. One of the acute responses is cardiac cell death that plays a critical role in the initiation and development of DCM. Besides hyperglycemia, inflammatory response in the diabetic heart is also a major cause for cardiac cell death. Diabetes or obesity often causes systemic and cardiac increases in tumor necrosis factor-alpha (TNFα), interleukin-18 and PAI-1. However, how these cytokines cause cardiac cell death remains unclear. It has been considered to relate to oxidative and/or nitrosative stress. Cardiac cell death is induced by the inflammatory cytokines that are increased in response to diabetes. Inflammatory cytokine-induced cardiac cell death is mediated by oxidative stress and is also the major initiator for DCM development [Wang, Y. H., and Cai, L. Diabetes/obesity-related inflammation, cardiac cell death and cardiomyopathy. *Zhong Nan Da Xue Xue Bao Yi Xue Ban* 2006, 31, 814-8].

AMP-activated protein kinase—The 5'-AMP-activated protein kinase (AMPK) functions as an intracellular fuel sensor that affects metabolism and gene expression in humans and rodents. AMPK has been described as an integrator of regulatory signals monitoring systemic and cellular energy status. Recently, it has been proposed that AMPK could provide a link in metabolic defects underlying progression to the metabolic syndrome. AMPK is a heterotrimeric enzyme complex consisting of a catalytic subunit alpha and two regulatory subunits beta and gamma. Rising AMP and falling ATP activate AMPK. AMP activates the system by binding to the gamma subunit that triggers phosphorylation of the catalytic alpha subunit by the upstream kinases LKB 1 and CaMKK-beta (calmodulin-dependent protein kinase kinase). The AMPK system is a regulator of energy balance that, once activated by low energy status, switches on ATP-producing catabolic pathways (such as fatty acid oxidation and glycolysis), and switches off ATP-consuming anabolic pathways (such as lipogenesis), both by short-term effect on phosphorylation of regulatory proteins and by long-term effect on gene expression (FIG. 3).

As well as acting at the level of the individual cell, the system also regulates food intake and energy expenditure at the whole body level, in particular by mediating the effects of insulin sensitizing adipokines leptin and adiponectin. AMPK is robustly activated during skeletal muscle contraction and myocardial ischemia playing a role in glucose transport and fatty acid oxidation. In liver, activation of AMPK results in enhanced fatty acid oxidation as well as decreased glucose production [Viollet, B., Mounier, R., Leclerc, J., Yazigi, A., Foretz, M., and Andreelli, F. Targeting AMP-activated protein kinase as a novel therapeutic approach for the treatment of metabolic disorders. *Diabetes Metab* 2007, 33, 395-402]. The net effect of AMPK activation is stimulation of hepatic fatty acid oxidation and ketogenesis, inhibition of cholesterol synthesis, lipogenesis, and triglyceride synthesis, inhibition of adipocyte lipolysis and lipogenesis, stimulation of skeletal muscle fatty acid oxidation and muscle glucose uptake, and modulation of insulin secretion by pancreatic beta-cells.

5-Aminoimidazole-4-carboxamide ribonucleoside (AICAR) represents a useful tool for identifying new target pathways and processes regulated by the AMPK protein kinase cascade. Incubation of rat hepatocytes with AICAR results in accumulation of the monophosphorylated derivative (5-aminoimidaz-ole-4-carboxamide ribonucleoside; ZMP) within the cell. ZMP mimics both activating effects of AMP on AMPK, i.e. direct allosteric activation and promotion of phosphorylation by AMPK kinase. Unlike existing methods for activating AMPK in intact cells (e.g. fructose, heat shock), AICAR does not perturb the cellular contents of ATP, ADP or AMP. Incubation of hepatocytes with AICAR activates AMPK due to increased phosphorylation, causes phosphorylation and inactivation of a known target for AMPK (3-hydroxy-3-methylglutaryl-CoA reductase), and almost total cessation of two of the known target pathways, i.e. fatty acid and sterol synthesis. Incubation of isolated adipocytes with AICAR antagonizes isoprenaline-induced lipolysis. This provides direct evidence that the inhibition by AMPK of activation of hormone-sensitive lipase by cyclic-AMP-dependent protein kinase, previously demonstrated in cell-free assays, also operates in intact cells.

AMPK also regulates food intake and energy expenditure at the whole body level, in particular by mediating the effects of insulin sensitizing adipokines leptin and adiponectin. AMPK is robustly activated during skeletal muscle contraction and myocardial ischemia playing a role in glucose transport and fatty acid oxidation.

Additional approaches to affect sustained weight loss in obese subjects represent a critical need. Further, compounds or formulations that safely and effectively activate AMPK may function to stimulate hepatic fatty acid oxidation and ketogenesis, inhibit cholesterol synthesis, lipogenesis, and triglyceride synthesis, inhibit adipocyte lipolysis and lipogenesis, stimulate of skeletal muscle fatty acid oxidation and muscle glucose uptake, and modulate insulin secretion by pancreatic beta-cells.

Inflammatory bowel disease—Each year inflammatory bowel diseases, such as Crohn's disease and ulcerative colitis, afflict more than one million people in the United States [Baumgart D C, Bernstein C N, Abbas Z, et al. IBD Around the world: Comparing the epidemiology, diagnosis, and treatment: Proceedings of the World Digestive Health Day 2010—Inflammatory bowel disease task force meeting. *Inflamm Bowel Dis* 2010]. The healthy gastrointestinal tract absorbs only the small molecules like those that are product of complete digestion. These molecules are the amino acids, simple sugars, fatty acids, vitamins, and minerals that the body requires for all the processes of life to function properly. The intestines, small intestine in particular, only allow these substances to enter the body due to the fact that the cells that make up the intestinal wall are tightly packed together. The intestines also contain special proteins called 'carrier proteins' that are responsible for binding to certain nutrients and transporting them through the intestinal wall and into the bloodstream.

Leaky Gut Syndrome (LGS) is common parlance for the disruption of the intestinal membrane integrity as a result of oxidative stressors or pro-inflammatory mediators, which compromise the ability of the intestinal wall to keep out large and undesirable molecules. Hence the name, as substances that are normally kept outside the body and within the intestines, are "leaking" across the intestinal wall and into the body as a whole. This happens when the spaces between the cells of the intestinal wall become enlarged for various reasons and allow larger, less digested particles and toxins to pass through—causing LGS. The body then recognizes these particles as foreign "invaders," and the immune system attempts to fight them off—which can set the stage for various autoimmune disorders.

This disruption of intestinal membrane integrity is applicable to the pathognomic impacts of asthma, arthritis, food allergies, ulcers, Crohn's disease, ulcerative colitis, celiac disease, autoimmune diseases, alcoholism, chronic fatigue, joint pain, migraines, diarrhea, parasitic infections, dysbiosis, candidiasis, multiple sclerosis, diabetes, multiple sclerosis, vasculitis, Addison's disease, lupus, thyroiditis, and fibromyalgia.

Novel, supercritical $CO_2$ extracts of *N. sativa* are described that contain from about 0.01 to about 39% (w/w) TQ and unexpectedly exhibit chemical and biological activities in vitro and clinically that differ both qualitatively and quantitatively from TQ, the putative active component of *N. sativa* seed extracts.

To date no process for supercritical extraction of *N. sativa* has been described that is useful for commercial quantities of ground seed. It is well known in the art, that changes in scale will profoundly affect the quality and quantity of the extract produced. The procedure described herein can be used in the extraction of commercial quantities of *N. sativa* seed in amounts greater than about 10 kg.

SUMMARY OF THE INVENTION

The present invention provides a method of making four commercial-scale compositions enriched in essential oils from seeds of *Nigella sativa* comprising the steps of: (i) grinding and sieving the seed of *Nigella sativa* to a fine powder about 20 to 30 mesh; (ii) extracting quantities of the ground seeds in amounts greater than 1 kg with supercritical $CO_2$ at about 140 bar, 50° C. for 30 minutes and collecting the fraction obtained; (iii) continuing the extraction at about 140 bar, 50° C. for 120 minutes and collecting the fraction obtained; (iv) increasing the pressure to about 300 bar, temperature to 60° C. and collection time to an additional 180 minutes and collecting the fraction obtained; and (v) formulating a fourth composition by mixing the extracted, spent *N. sativa* powdered seeds with the essential oil fraction collected at about 300 bar, 60° C. and 180 minutes in a ratio of about 24:1.

The present invention further provides four novel, supercritical $CO_2$ extracts of ground seeds obtained from *N. sativa* produced on a commercial scale. The novel compositions thus produced can be used (i) to reduce oxidative stress, (ii) to inhibit excessive prostate specific antigen secretion from precancerous prostate cells, (iii) to uncouple mitochondrial membrane potential in adipocytes, (iv) to inhibit iNOS mediated NO production in adipocytes and myocytes from multiple cytokine stimulation simultaneously, (v) to increase lipolysis in adipocytes and myocytes, (v) to activate AMPK in myocytes, (vi) to overcome adaptive thermogenesis in humans resulting in more effective weight loss with exercise, (vii) to reduce inflammatory and oxidative loss of intestinal membrane integrity, and (viii) to attenuate t10-CLA mediated pro inflammatory effects on adipocyte secretion of IL-6 and adiponectin.

The present invention further provides a method of treating diseases or pathologies related to oxidative stress, inflammation, metabolic syndrome, type 1 or type 2 diabetes, and obesity in an animal comprising administering to an animal exhibiting signs, signalments, or symptoms of the pathology or disease an effective amount of the supercritical extract and continuing the administration of the composition until the signs, signalments or symptoms are reduced.

The present invention relates to the unexpected discovery that certain super critical fluid $CO_2$ extracts of *N. sativa* decrease mitochondrial membrane potential in adipocytes implying decreased ATP synthesis and increased thermogenesis. The invention provides methods for modifying adipocyte or myocyte physiology in a subject, comprising administering to the subject a pharmaceutical composition of a supercritical fluid extract of *N. sativa* or mixtures thereof. Preferred embodiments provide compositions and methods for enhancing adipocyte thermogenesis or decreasing oxidative stress utilizing supercritical fluid extracts of *N. sativa*.

Further, the present invention relates to the unexpected discovery that certain super critical fluid extracts of *N. sativa* inhibit iNOS-mediated NO biosynthesis as a result of the action of multiple external stimuli to adipocytes or myocytes implying inhibition of protein nitrosylation.

Additionally, the present invention relates to the unexpected discovery that certain super critical fluid extracts of *N. sativa* dramatically activate AMPK implying stimulation of hepatic fatty acid oxidation and ketogenesis, inhibition of cholesterol synthesis, lipogenesis, and triglyceride synthesis, inhibition of adipocyte lipolysis and lipogenesis, stimulation of skeletal muscle fatty acid oxidation and muscle glucose uptake, and modulation of insulin secretion by pancreatic beta-cells.

DETAILED DESCRIPTION OF THE INVENTION

Figure 1:
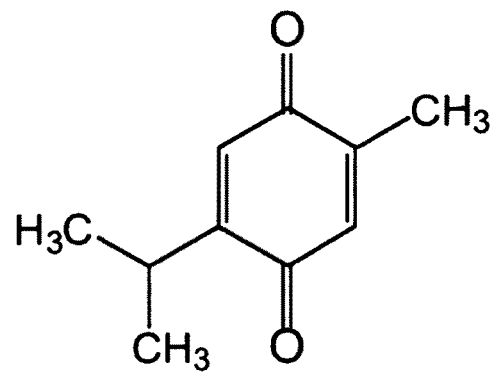
FIG. 1 is the structure of [A] thymoquinone and [B] dithymoquinone.
Figure 1:
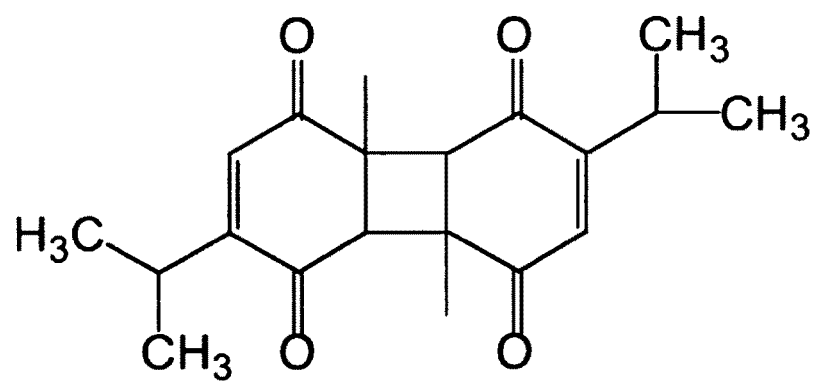
Figure 2:
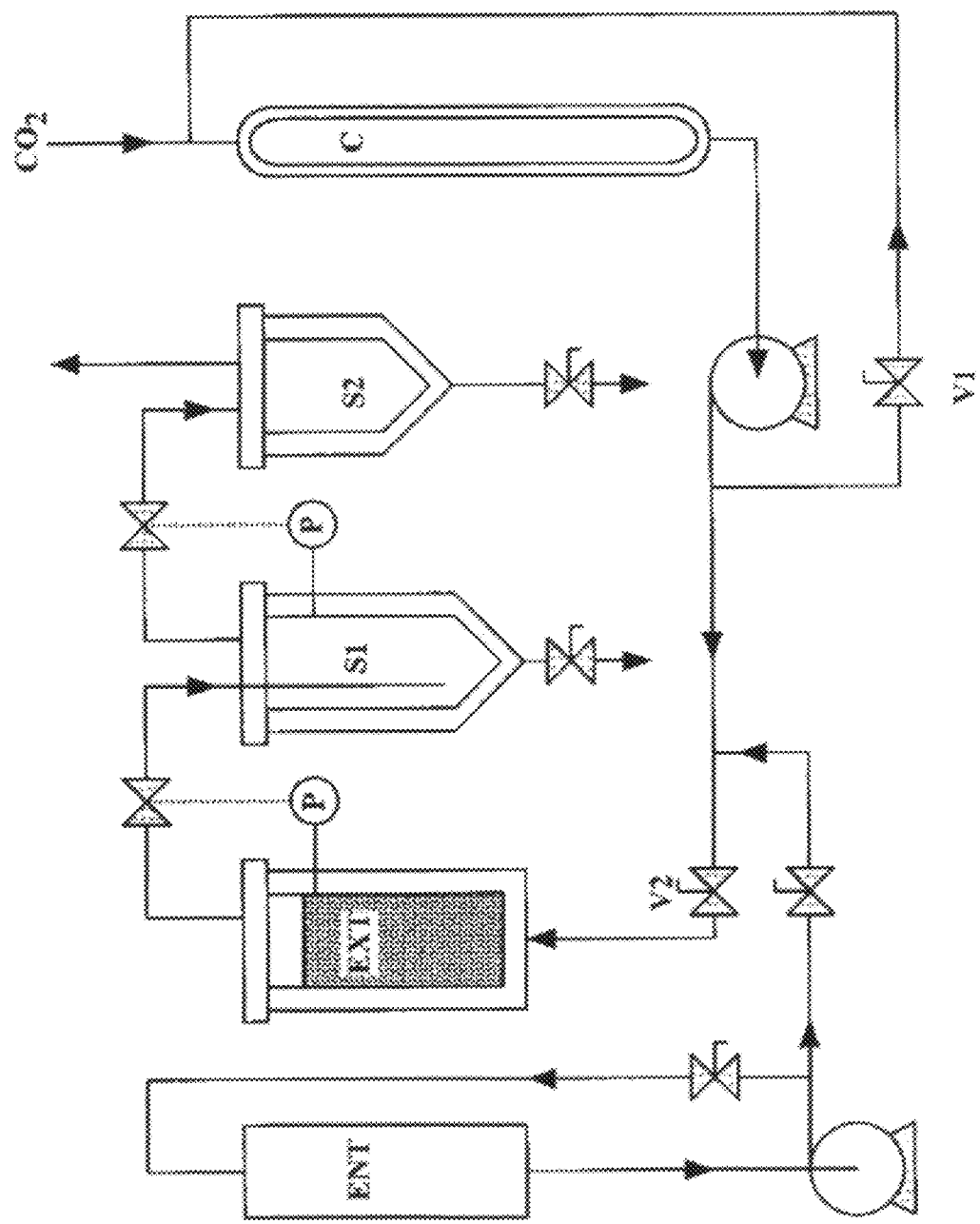
FIG. 2 is a schematic diagram of the supercritical $CO_2$ extraction circuit used in Example 1.

The compositions of the invention includes four, unique supercritical fluid extracts of *N. sativa* containing concentrations of the TQ marker compound ranging from about 0.01 to about 40%. These compositions may be used for their antioxidant or anti-inflammatory properties. The resulting compositions can be consumed as a dietary supplement to address the risk factors associated with oxidative stress, benign prostate hyperplasia, obesity, metabolic syndrome, diabetes, increasing exercise endurance or other inflammatory-based pathologies.

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of recombinant DNA technology include Sambrook et al., Molecular Cloning: A Laboratory Manual, 2nd Ed., Cold Spring Harbor Laboratory Press, New York (1989); Kaufman et al., Eds., Handbook of Molecular and Cellular Methods in Biology in Medicine, CRC Press, Boca Raton (1995); McPherson, Ed., Directed Mutagenesis: A Practical Approach, IRL Press, Oxford (1991). Standard reference works setting forth general definitions of medical terms and the general principles of pharmacology, respectively, include Stedman's Medical Dictionary [$26^{th}$ edition] and Goodman and Gilman's The Pharmacological Basis of Therapeutics, 11th Ed., McGraw Hill Companies Inc., New York (2006).

In the specification and the appended claims, the singular forms include plural referents unless the context clearly dictates otherwise. As used in this specification, the singular forms "a," "an" and "the" specifically also encompass the plural forms of the terms to which they refer, unless the content clearly dictates otherwise. Additionally, as used herein, unless specifically indicated otherwise, the word "or" is used in the "inclusive" sense of "and/or" and not the "exclusive" sense of "either/or." The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable that is inherently discrete, the variable can be equal to any integer value of the numerical range, including the end-points of the range. Similarly, for a variable that is inherently continuous, the variable can be equal to any real value of the numerical range, including the end-points of the range. As an example, a variable that is described as having values between 0 and 2 can be 0, 1 or 2 for variables that are inherently discrete, and can be 0.0, 0.1, 0.01, 0.001, or any other real value for variables that are inherently continuous.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or compounds, but may also include additional features or compounds.

Reference is made hereinafter in detail to specific embodiments of the invention. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail, in order not to unnecessarily obscure the present invention.

Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The term "treat" and its verbal variants refer to palliation or amelioration of an undesirable physiological state. Thus, for example, where the physiological state is poor glucose tolerance, "treatment" refers to improving the glucose tolerance of a treated subject. As another example, where the physiological state is obesity, the term "treatment" refers to reducing the body fat mass, improving the body mass or improving the body fat ratio of a subject. Treatment of diabetes means improvement of blood glucose control. Treatment of inflammatory diseases means reducing the inflammatory response either systemically or locally within the body. Treatment of osteoporosis means an increase in the density of bone mineralization or a favorable change in metabolic or systemic markers of bone mineralization. The person skilled in the art will recognize that treatment may, but need not always, include remission or cure.

The term "prevent" and its variants refer to prophylaxis against a particular undesirable physiological condition. The prophylaxis may be partial or complete. Partial prophylaxis may result in the delayed onset of a physiological condition. The person skilled in the art will recognize the desirability of delaying onset of a physiological condition, and will know to administer the compositions of the invention to subjects who are at risk for certain physiological conditions in order to delay the onset of those conditions. For example, the person skilled in the art will recognize that obese subjects are at elevated risk for coronary artery disease. Thus, the person skilled in the art will administer compositions of the invention in order to increase insulin sensitivity in an obese, whereby the onset of diabetes mellitus or dyslipemia may be prevented entirely or delayed.

As used herein "adaptive thermogenesis" represents the decrease in energy expenditure beyond what could be predicted from the changes in fat mass or fat-free mass under conditions of standardized physical activity in response to a decrease in energy intake.

As used herein the term "oxidative stress" is used to describe the effect of oxidation in which an abnormal level of reactive oxygen species (ROS), such as the free radicals (e.g. hydroxyl, nitric acid, superoxide) or the non-radicals (e.g. hydrogen peroxide, lipid peroxide) lead to damage (called oxidative damage) to specific molecules with consequential injury to cells or tissue. Increased production of ROS occurs as a result of fungal or viral infection, inflammation, ageing, UV radiation, pollution, excessive alcohol consumption, cigarette smoking, etc. Removal or neutralization of ROS is achieved with antioxidants, endogenous (e.g. catalase, glutathione, superoxide dismutase) or exogenous (e.g. vitamins A, C, E, bioflavonoids, carotenoids). Oxidative damage to the eye, particularly the retina and the lens, is a contributing factor to age-related macular degeneration and cataract.

All forms of life maintain a reducing environment within their cells. This reducing environment is preserved by enzymes that maintain the reduced state through a constant input of metabolic energy. Disturbances in this normal redox state can cause toxic effects through the production of peroxides and free radicals that damage all components of the cell, including proteins, lipids and DNA.

In humans, oxidative stress is involved in the etiology of many diseases, such as atherosclerosis, type 1 and type 2 diabetes, Parkinson's disease, cardiac arrest, myocardial infarction, Alzheimer's disease, Fragile X syndrome and chronic fatigue syndrome. Short-term oxidative stress, however, may also be important in prevention of aging by induction of a process named mitohormesis. ROS can be beneficial, as they are used by the immune system as a way to attack and kill invading pathogens. ROS are also used in cell signaling. This is dubbed redox signaling and is a critical component of such pathognomic conditions as obesity, metabolic syndrome, colitis, irritable bowel syndrome and adaptive thermogenesis.

The methods of the present invention are intended for use with any subject that may experience the benefits of the methods of the invention. Thus, in accordance with the invention, "subjects" include humans as well as non-human subject, particularly domesticated animals. It will be understood that the subject to which a compound of the invention is administered need not suffer from a specific traumatic state. Indeed, the compounds of the invention may be administered prophylactically, prior to any development of symptoms. The term "therapeutic," "therapeutically," and permutations of these terms are used to encompass therapeutic, palliative as well as prophylactic uses.

As used herein, the term "solvent" refers to a liquid of gaseous, aqueous or organic nature possessing the necessary characteristics to extract solid material from the hop plant product. Examples of solvents would include, but not limited to, water, steam, superheated water, methanol, ethanol, hexane, chloroform, liquid $CO_2$, liquid $N_2$, propane, or any combinations of such materials.

As used herein, the term "$CO_2$ extract" refers to the solid material resulting from exposing more than 10 kg powdered N. sativa seeds to a liquid or supercritical $CO_2$ preparation followed by subsequent removal of the $CO_2$.

As used herein, "decreased secretion or biosynthesis," means to decrease by at least 3%, the rate of secretion or amount of biosynthesis of the referent compound. The invention further provides a method of decreasing adipocyte or myocyte concentrations of inflammatory mediators in a subject, comprising administering to the subject an amount of the composition sufficient to decrease NO secretion from adipocytes or myocytes in the subject. In general, a decrease in adipocyte or myocyte NO secretion or biosynthesis will result in improvements in such conditions as obesity, metabolic syndrome, colitis, irritable bowel syndrome and adaptive thermogenesis.

As used herein, "linear inhibitory effect" refers to a linear decrease in secretion or biosynthesis resulting from all concentrations of the inhibiting material over a dose-response curve. For example, inhibition at low concentrations followed by a failure of inhibition or increased secretion at higher concentrations represents a lack of a linear inhibitory effect.

As used herein, "Leaky Gut Syndrome (LGS)" is an increase in permeability of the intestinal mucosa to luminal macromolecules, antigens and toxins associated with inflammatory degenerative and/or atrophic mucosal damage. LGS can lead to any number of seemingly unrelated symptoms affecting every organ system in the body. LGS has also been linked with having a causative role in a large number of distinct illnesses. Many of these are autoimmune diseases, which means the immune system attacks the body's own cells. LGS plays a role in these types of illness because it increases immune reactions to food particles and then cross reactivity may occur meaning that the immune system attacks body tissues that are chemically similar to the foods to which it has become sensitized. A sampling of the many diseases in which leaky gut syndrome may have a role includes: rheumatoid arthritis, osteoarthritis, asthma, multiple sclerosis, vasculitis, Crohn's Disease, colitis, Addison's Disease, lupus, thyroiditis, chronic fatigue syndrome, and fibromyalgia.

As used herein, the term "CLA isomers" refers to fatty acids with the same 18-carbon, polyunsaturated structure. In the case of CLA, each isomer is derived from the 18-carbon essential polyunsaturated fat linoleic acid (18:2n-6), which has two cis-double bonds at carbons 9 and 12. Cis9-CLA has been shown to regulate adiposity in animals and humans. The trans10-CLA isomer (t10-CLA), however, is associated with hyperglycemia, insulin resistance and dyslipidemia as well as elevated levels of inflammatory prostaglandins and cytokines. These stressors can impair the adipocyte's ability to synthesize or store fatty acids as triglycerides, causing lipids to accumulate in hepatocytes and myocytes and resulting in steatosis and insulin resistance, respectively. These issues raise concern about the safe and effective use of supplements containing t10-CLA as a dietary strategy for weight loss.

In some aspects the compositions further comprise a pharmaceutically acceptable excipient where the pharmaceutically acceptable excipient is selected from the group consisting of coatings, isotonic and absorption delaying agents, binders, adhesives, lubricants, disintergrants, coloring agents, flavoring agents, sweetening agents, absorbants, detergents, and emulsifying agents. In yet further aspects, the composition additionally comprises one or more members selected from the group consisting of antioxidants, vitamins, minerals, proteins, fats, and carbohydrates.

The term "therapeutically effective amount" is used to denote treatments at dosages effective to achieve the therapeutic result sought. Furthermore, one of skill will appreciate that the therapeutically effective amount of the compound of the invention may be lowered or increased by fine-tuning and/or by administering more than one compound of the invention, or by administering a compound of the invention with another compound. See, for example, Meiner, C. L., "Clinical Trials: Design, Conduct, and Analysis," Monographs in Epidemiology and Biostatistics, Vol. 8 Oxford University Press, USA (1986). The invention therefore provides a method to tailor the administration/treatment to the particular exigencies specific to a given mammal. As illustrated in the following examples, therapeutically effective amounts may be easily determined, for example, empirically by starting at relatively low amounts and by step-wise increments with concurrent evaluation of beneficial effect.

As used herein, "more effectively" is used to describe relative biological responses of compounds or formulations wherein the response elicited by one formulation is greater per unit dose than the other.

The term "pharmaceutically acceptable" is used in the sense of being compatible with the other ingredients of the compositions and not deleterious to the recipient thereof.

As used herein, "compounds" may be identified either by their chemical structure, chemical name, or common name. When the chemical structure and chemical or common name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated or identified compounds. The compounds described also encompass isotopically labeled compounds where one or more atoms have an atomic mass different from the atomic mass conventionally found in nature. Examples of isotopes that may be incorporated into the compounds of the invention include, but are not limited to, $^2H$, $^3H$, $^{13}C$, $^{14}C$, $^{15}N$, $^{18}O$, $^{17}O$, etc. Compounds may exist in unsolvated forms as well as solvated forms, including hydrated forms and as N-oxides. In general, compounds may be hydrated, solvated or N-oxides. Certain compounds may exist in multiple crystalline or amorphous forms. Also contemplated within the scope of the invention are congeners, analogs, hydrolysis products, metabolites and precursor or prodrugs of the compound. In general, all physical forms are equivalent for the uses contemplated herein and are intended to be within the scope of the present invention.

The compounds according to the invention are optionally formulated in a pharmaceutically acceptable vehicle with any of the well-known pharmaceutically acceptable carriers, including diluents and excipients (see Remington's Pharmaceutical Sciences, 18th Ed., Gennaro, Mack Publishing Co., Easton, Pa. 1990 and Remington: The Science and Practice of Pharmacy, Lippincott, Williams & Wilkins, 1995). While the type of pharmaceutically acceptable carrier/vehicle employed in generating the compositions of the invention will vary depending upon the mode of administration of the composition to a mammal, generally pharmaceutically acceptable carriers are physiologically inert and non-toxic. Formulations of compositions according to the invention may contain more than one type of compound of the invention), as well any other pharmacologically active ingredient useful for the treatment of the symptom/condition being treated.

The compounds of the present invention may be provided in a pharmaceutically acceptable vehicle using formulation methods known to those of ordinary skill in the art. The compositions of the invention can be administered by standard routes. The compositions of the invention include those suitable for oral, inhalation, rectal, ophthalmic (including intravitreal or intracameral), nasal, topical (including buccal and sublingual), vaginal, or parenteral (including subcutaneous, intramuscular, intravenous, intradermal, and intratracheal). In addition, polymers may be added according to standard methodologies in the art for sustained release of a given compound.

It is contemplated within the scope of the invention that compositions used to treat a disease or condition will use a pharmaceutical grade compound and that the composition will further comprise a pharmaceutically acceptable carrier. It is further contemplated that these compositions of the invention may be prepared in unit dosage forms appropriate to both the route of administration and the disease and patient to be treated. The compositions may conveniently be presented in dosage unit form be prepared by any of the methods well known in the art of pharmacy. All methods include the step of bringing the active ingredient into association with the vehicle that constitutes one or more auxiliary constituents. In general, the compositions are prepared by uniformly and intimately bringing the active ingredient into association with a liquid vehicle or a finely divided solid vehicle or both, and then, if necessary, shaping the product into the desired composition.

The term "dosage unit" is understood to mean a unitary, i.e. a single dose which is capable of being administered to a patient, and which may be readily handled and packed, remaining as a physically and chemically stable unit dose comprising either the active ingredient as such or a mixture of it with solid or liquid pharmaceutical vehicle materials.

Compositions suitable for oral administration may be in the form of discrete units as capsules, sachets, tablets, soft gels or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, gum arabic, dextran, sodium carboxymethylcellulose, gelatin, methylcellulose and polyvinylpyrrolidone. The active ingredient may also be administered in the form of a bolus, electuary or paste.

In addition to the compositions described above, the compositions of the invention may also be formulated as a depot preparation. Such long-acting compositions may be administered by implantation (e.g. subcutaneously, intraabdominally, or intramuscularly) or by intramuscular injection. Thus, for example, the active ingredient may be formulated with suitable polymeric or hydrophobic materials (for example, as an emulsion in a pharmaceutically acceptable oil), or an ion exchange resin.

The compounds of this invention either alone or in combination with each other or other compounds generally will be administered in a convenient composition. The following representative composition examples are illustrative only and are not intended to limit the scope of the present invention. In the compositions that follow, "active ingredient" means a compound of this invention.

As used herein, "therapeutically effective time window" means the time interval wherein administration of the compounds of the invention to the subject in need thereof reduces or eliminates the deleterious effects or symptoms. In a preferred embodiment, the compound of the invention is administered proximate to the deleterious effects or symptoms.

*Nigella sativa* Linn. (family: Ranunculaceae), commonly known as black seed or black curcumin, is an annual plant that has been traditionally used in the Indian subcontinent, Arabian countries, and Europe for culinary and medicinal purposes as a natural remedy for a number of illnesses and conditions that include asthma, hypertension, diabetes, inflammation, cough, bronchitis, headache, eczema, fever, dizziness and influenza. The seeds or its oil are used as a carminative, diuretic, lactoagogue, and vermifuge. They are also used in food as a spice and a condiment.

*N. sativa* seeds contain 36-38% fixed oils, proteins, alkaloids, saponin and 0.4-2.5% essential oil. The fixed oil is composed mainly of unsaturated fatty acids, including the unusual C20:2 arachidic and eiosadienoic acids. Major components of the essential oil include thymoquinone (27-57%), p-cymene (7.1-15.5%), carvacrol (5.8-11.6%), trans-anethole (0.25-2.3%) p-terpineol (2.0-6.6%) and longifoline (1.0-8.0%). TQ readily dimerizes to form dithymoquinone and as used herein, TQ will also refer to the naturally occurring dimmer dithymoquinone.

Many studies have been conducted, particularly during the past two decades, on the effect of *N. sativa* seed extracts on various body systems in vivo or in vitro. Included among those physiological variables studied are antioxidant, anti-inflammatory and analgesic actions, anticarcinogenic activity, hypotensive, antidiabetic, antiulcer, antimicrobial and antiparasitic responses [Ali B H, Blunden G. 2003. Pharmacological and toxicological properties of *Nigella sativa*. *Phytother Res* 17: 299-305]. This body of research teaches that extraction methodology is a primary determinant of the effectiveness of the resulting *N. sativa* seed extract [see for example: Kokoska, L., J. Havlik, et al. (2008). "Comparison of chemical composition and antibacterial activity of *Nigella sativa* seed essential oils obtained by different extraction methods." *J Food Prot* 71(12): 2475-2480].

Recently studies have been reported using supercritical liquid extracts of *N. sativa* seeds containing 2.0 to 2.8 percent TQ, but none with extracts produced under the conditions of pressure, temperature and time as described herein. Further, biological activities of extracts in these and other studies with organic solvent extraction were roughly equal to their TQ content and none of the reported studies were applicable to commercially-scaled quantities of *N. sativa* extract [Ismail, M., G. Al-Naqeep, et al. (2010). "*Nigella sativa* thymoquinone-rich fraction greatly improves plasma antioxidant capacity and expression of antioxidant genes in hypercholesterolemic rats." *Free Radic Biol Med* 48(5): 664-672; Al-Naqeep, G., M. Ismail, et al. (2009). "Regulation of Low-Density Lipoprotein Receptor and 3-Hydroxy-3-Methylglutaryl Coenzyme A Reductase Gene Expression by Thymoquinone-Rich Fraction and Thymoquinone in HepG2 Cells." *J Nutrigenet Nutrigenomics* 2(4-5): 163-172].

As used herein, "commercial-scale quantities" of *N. sativa* seed are considered quantities of raw material in excess of about 10 kg. All supercritical fluid extraction herein refers to extraction of commercial-scale quantities of *N. sativa* powdered seed.

All prior art, including reports using supercritical extraction of about 100 g or less of *N. sativa*, teach that TQ is the active component of *N. sativa*. The present application, however, teaches that certain supercritical $CO_2$ extracts produced at pressures below 600 bar extract TQ more efficiently and exhibit unexpected potency greater than their TQ content. Additionally, the present application teaches that when commercial volumes of *N. sativa* seeds are extracted, supercritical $CO_2$ extracts can be enriched with TQ using lower pressures without subsequent extraction steps.

The present compositions can be provided in any convenient form. It can be provided as dietary supplement in capsule or tablet form. It can be formulated into a food or drink, and provided, for example, as a snack bar, a cereal, a drink, a gum, or in any other easily ingested form. It can also be provided as a cream or lotion for topical application. One trained in the art can readily formulate the present composition into any of these convenient forms for oral or topical administration.

The amount of other additives per unit serving are a matter of design and will depend upon the total number of unit servings of the nutritional supplement daily administered to the patient. The total amount of other ingredients will also depend, in part, upon the condition of the patient. Preferably, the amount of other ingredients will be a fraction or multiplier of the RDA or DRI amounts. For example, the nutritional supplement will comprise 50% RDI (Reference Daily Intake) of vitamins and minerals per unit dosage and the patient will consume two units per day.

Flavors, coloring agents, spices, nuts and the like can be incorporated into the product. Flavorings can be in the form of flavored extracts, volatile oils, chocolate flavorings (e.g., non-caffeinated cocoa or chocolate, chocolate substitutes such as carob), peanut butter flavoring, cookie crumbs, crisp rice, vanilla or any commercially available flavoring. Flavorings can be protected with mixed tocopherols. Examples of useful flavorings include but are not limited to pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, cherry oil, walnut oil, cinnamon oil, clove oil, or peppermint oil; peanut butter, chocolate flavoring, vanilla cookie crumb, butterscotch or toffee. In a preferred embodiment, the nutritional supplement contains berry or other fruit flavor. The food compositions may further be coated, for example with a yogurt coating if it is as a bar.

Emulsifiers may be added for stability of the final product. Examples of suitable emulsifiers include, but are not limited to, lecithin (e.g., from egg or soy), or mono- and di-glycerides. Other emulsifiers are readily apparent to the skilled artisan and selection of suitable emulsifier(s) will depend, in part, upon the formulation and final product.

Preservatives may also be added to the nutritional supplement to extend product shelf life. Preferably, preservatives such as potassium sorbate, sodium sorbate, potassium benzoate, sodium benzoate or calcium disodium EDTA are used.

In addition to the carbohydrates described above, the nutritional supplement can contain natural or artificial sweeteners, e.g., glucose, sucrose, fructose, saccharides, cyclamates, aspartamine, sucralose, aspartame, acesulfame K, or sorbitol.

Manufacture of the Preferred Embodiments—The nutritional supplements of the present invention may be formulated using any pharmaceutically acceptable forms of the vitamins, minerals and other nutrients discussed above, including their salts. They may be formulated into capsules, tablets, powders, suspensions, gels or liquids optionally comprising a physiologically acceptable carrier, such as but not limited to water, milk, juice, soda, starch, vegetable oils, salt solutions, hydroxymethyl cellulose, carbohydrate. In a preferred embodiment, the nutritional supplements may be formulated as powders, for example, for mixing with consumable liquids, such as milk, juice, sodas, water or consumable gels or syrups for mixing into other nutritional liquids or foods. The nutritional supplements of this invention may be formulated with other foods or liquids to provide pre-measured supplemental foods, such as single serving beverages or bars, for example.

In a particularly preferred embodiment, the nutritional supplement will be formulated into a nutritional beverage, a form that has consumer appeal, is easy to administer and incorporate into one's daily regimen, thus increasing the chances of patient compliance. To manufacture the beverage, the ingredients are dried and made readily soluble in water. For the manufacture of other foods or beverages, the ingredients comprising the nutritional supplement of this invention can be added to traditional formulations or they can be used to replace traditional ingredients. Those skilled in food formulating will be able to design appropriate foods or beverages with the objective of this invention in mind.

The nutritional supplement can be made in a variety of forms, such as puddings, confections, (i.e., candy), nutritional beverages, ice cream, frozen confections and novelties, or non-baked, extruded food products such as bars. The preferred form is a powder to add to a beverage or a non-baked extruded nutritional bar. In another embodiment, the ingredients can be separately assembled. For example, certain of the ingredients (e.g., the conjugated fatty acids or alcohols and thiol compounds) can be assembled into a tablet or capsule using known techniques for their manufacture. The remaining ingredients can be assembled into a powder or nutritional bar. For the manufacture of a food bar, the dry ingredients are added with the liquid ingredients in a mixer and mixed until the dough phase is reached; the dough is put into an extruder and extruded; the extruded dough is cut into appropriate lengths; and the product is cooled. The two assembled forms comprise the nutritional supplement and can be packaged together or separately, such as in the form of a kit, as described below. Further, they can be administered together or separately, as desired.

Use of Preferred Embodiments—The preferred embodiments contemplate treatment of disorders related to oxidative stress, inflammation, metabolic syndrome, all forms of diabetes, and obesity. A pharmaceutically acceptable carrier may also be used in the present compositions and formulations. The recommended daily amounts of each ingredient, as described above, serve as a guideline for formulating the nutritional supplements of this invention. The actual amount of each ingredient per unit dosage will depend upon the number of units administered daily to the individual in need thereof. This is a matter of product design and is well within the skill of the nutritional supplement formulator.

The ingredients can be administered in a single formulation or they can be separately administered. For example, it may be desirable to administer the compounds in a form that masks their taste (e.g., capsule or pill form) rather than incorporating them into the nutritional composition itself (e.g., powder or bar). Thus, the invention also provides a pharmaceutical pack or kit comprising one or more containers filled with one or more of the ingredients of the nutritional compositions of the invention (e.g., nutritional supplement in the form of a powder and capsules containing TQ and/or synephrine). Optionally associated with such container(s) can be a notice in the form prescribed by a government agency regulating the manufacture, use or sale of pharmaceutical products, which notice reflects approval by the agency of manufacture, use of sale for human administration. The pack or kit can be labeled with information regarding mode of administration, sequence of administration (e.g., separately, sequentially or concurrently), or the like. The pack or kit may also include means for reminding the patient to take the therapy. The pack or kit can be a single unit dosage of the combination therapy or it can be a plurality of unit dosages. In particular, the agents can be separated, mixed together in any combination, present in a formulation or tablet.

The preferred embodiments provide compositions and methods to promote normal adipocyte or myocyte function. All preferred embodiments provide varying amounts of *N. sativa* essential oil containing from about 0.01 to 39% (w/w) TQ as a marker compound. Generally the formulations comprise supercritical $CO_2$ extracts of ground *N. sativa* seeds. In one embodiment, the composition comprises a supercritical $CO_2$-extracted fraction of ground N sativa seeds initially extracted at 140 bar, 50° C. and 30 minutes.

A second embodiment comprises a supercritical $CO_2$-extracted fraction of ground *N. sativa* seeds extracted at 140 bar, 50° C. and 120 minutes following the removal of the first fraction. A third embodiment comprises a supercritical $CO_2$-extracted fraction of ground *N. sativa* seeds extracted at 300 bar, 60° C. and 180 minutes following the removal of the second fraction.

Finally, a fourth embodiment comprises the combination resulting from the addition of the third fraction to the spent, extracted ground seed in a ratio of 1:24 (Extract:Spent Seed Powder).

EXAMPLES

Example 1

Efficiency of Supercritical Fluid Extraction of *Nigella sativa* from Research-Scale (100 g) and Commercial-Scale (100 kg) Quantities of Powdered Seeds Objective—The first objective of this experiment was to compare the extraction efficiency of supercritical $CO_2$ extraction of powdered *N. sativa* seeds under research conditions, defined as amounts of about 100 g, with the extraction efficiency under commercial-scale conditions, defined as amounts of about 100 kg. A second objective was to produce four supercritical $CO_2$ extracts of *N. sativa* seeds obtained under various conditions of pressure, temperature and time from commercial-scale quantities. To date, no supercritical extraction procedure has demonstrated the ability to process commercial quantities (1-100 kg) of powdered seed that contain concentrations of TQ above 10 percent without further extraction steps. It is well known in the art that scale of the extraction process can greatly affect the components of the extract and that extraction results obtained with small quantities of substrate do not reflect results obtained with larger, commercial quantities.

As TQ is widely considered the putative active compound in *N. sativa* essential oil, the TQ content of each of the fractions was used for comparing the efficiency of the supercritical extraction process under research and commercial conditions. Additionally, the use of the TQ standard allows for comparison to prior art.

Raw material purchase—The black seeds of *N. sativa* are seasonal, available from April to June of every year. The main source is in northern parts of India particularly in Uttar Pradesh. Stocked material is available through out the year. The cost generally fluctuates between $2.5/kg to $ 5.0/kg.

Grinding and sieving—Once the 110 kg of *N. sativa* seeds was purchased it was ground to a fine powder between 20-30 mesh. A magnetic screening system was used to ensure removal of metallic impurities, particularly iron.

Figure 3:
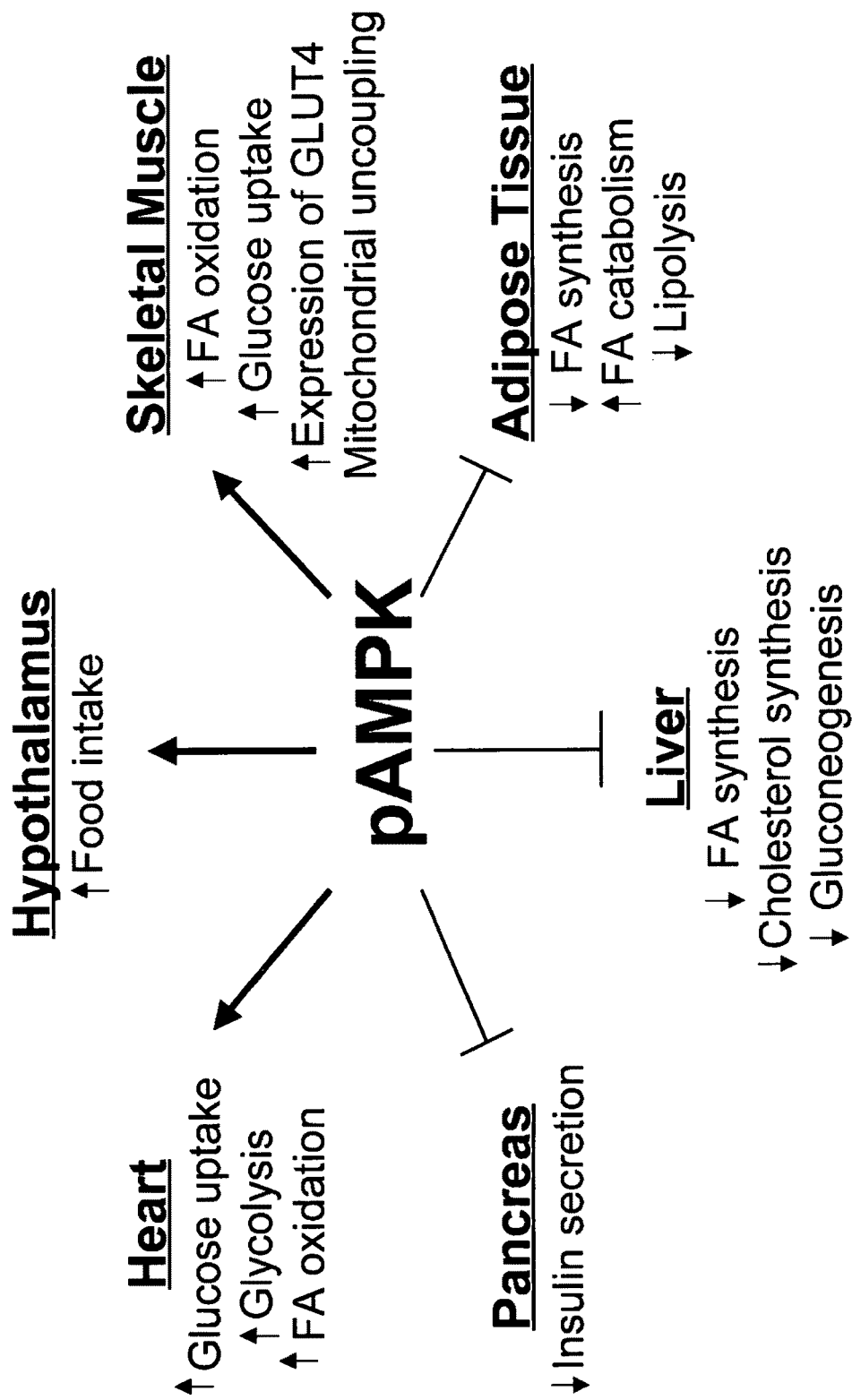
FIG. 3 depicts the role of AMPK in regulating energy balance at the whole-body level. Arrows indicate positive effects, and bars indicate negative effects. FA=fatty acid.

Supercritical fluid extraction—In this example, the process conditions during the extraction of N saliva seeds with supercritical $CO_2$ extraction were varied with respect to pressure, temperature and time (Table 2). The commercial-scale extraction was performed in a polyvalent pilot plant extraction set-up shown schematically in FIG. 3. Liquid $CO_2$ entering the apparatus was cooled in condenser C before it was pressurized and passed into the system. The flow rate was adjusted manually before the experiment. During the extraction process, the temperatures of the extractor, $CO_2$, and separators 1 and 2 (S1/S2) were automatically regulated through the recirculation of thermostatic water from three individually regulated water baths. Supercritical $CO_2$ extraction under research conditions was performed using a laboratory-scale SFE apparatus (100 mL up to 10 L systems). Extraction conditions and processes were similar for both commercial and research scaling as follows.

The ground *N. sativa* seeds were loaded into a cylindrical container that was equipped with steel mesh filters on both ends, thus enabling $CO_2$ to pass the cylinder without transport of solids to the exterior. After prepressurization of the total system and the regulation of the $CO_2$ flow rate, the extractor (EXT) was depressurized and the cylinder was subsequently placed inside the extractor, after which the complete $CO_2$ flow was redirected toward the extractor using valves V1 and V2. The temperature/pressure combinations of both separator vessels S1 and S2 were controlled individually. The extraction was stopped by redirecting the $CO_2$ flow again to recirculation over the condenser. The solid residue was removed from the extractor after stepwise depressurization of the entire system. Subsequently, both separator vessels were rinsed with hexane, and extracts were collected in UV-opaque bottles to prevent UV-activated degradation of the extract. Pressure/temperature combinations and extraction times for the extracts produced (NS8-NS10) are presented in Table 2.

Thymoquinone concentration—TQ content of the various fractions obtained were determined by HPLC analysis as described by Ghosheh (Ghosheh O A, Houdi A A, Crooks P A. High performance liquid chromatographic analysis of the pharmacologically active quinones and related compounds in the oil of the black seed (*Nigella sativa* L.). *J Pharm Biomed Anal*. April 1999; 19(5):757-762) with no modifications.

Results—Seven fractions 1, 2, 3, 4, 5, 6 and 7 were initially collected during the three-hour extraction process. Fractions 1, 2, 3 and 4, which were collected over 30 minutes at 140 bar and 50° C. in Sep 1, were combined to produce the fraction termed NS8 with a TQ content, respectively, of 5.47% and 2.24% for research and commercial-scale extraction. The fifth working fraction, which was collected over the next two-hours at 140 bar and 50° C. in Sep 2, was termed NS9 and contained, respectively, 2.95% and 39.3% TQ % for research and commercial-scale extraction.

Following extraction at 140 bar and 50° C., the pressure was increased to 300 bar and temperature to 60° C. over three hours producing fractions 6 and 7 that were combined to form fraction NS10 with a TQ content for research and commercial scale of 1.29% and 0.24%, respectively (Table 2).

Figure 4:
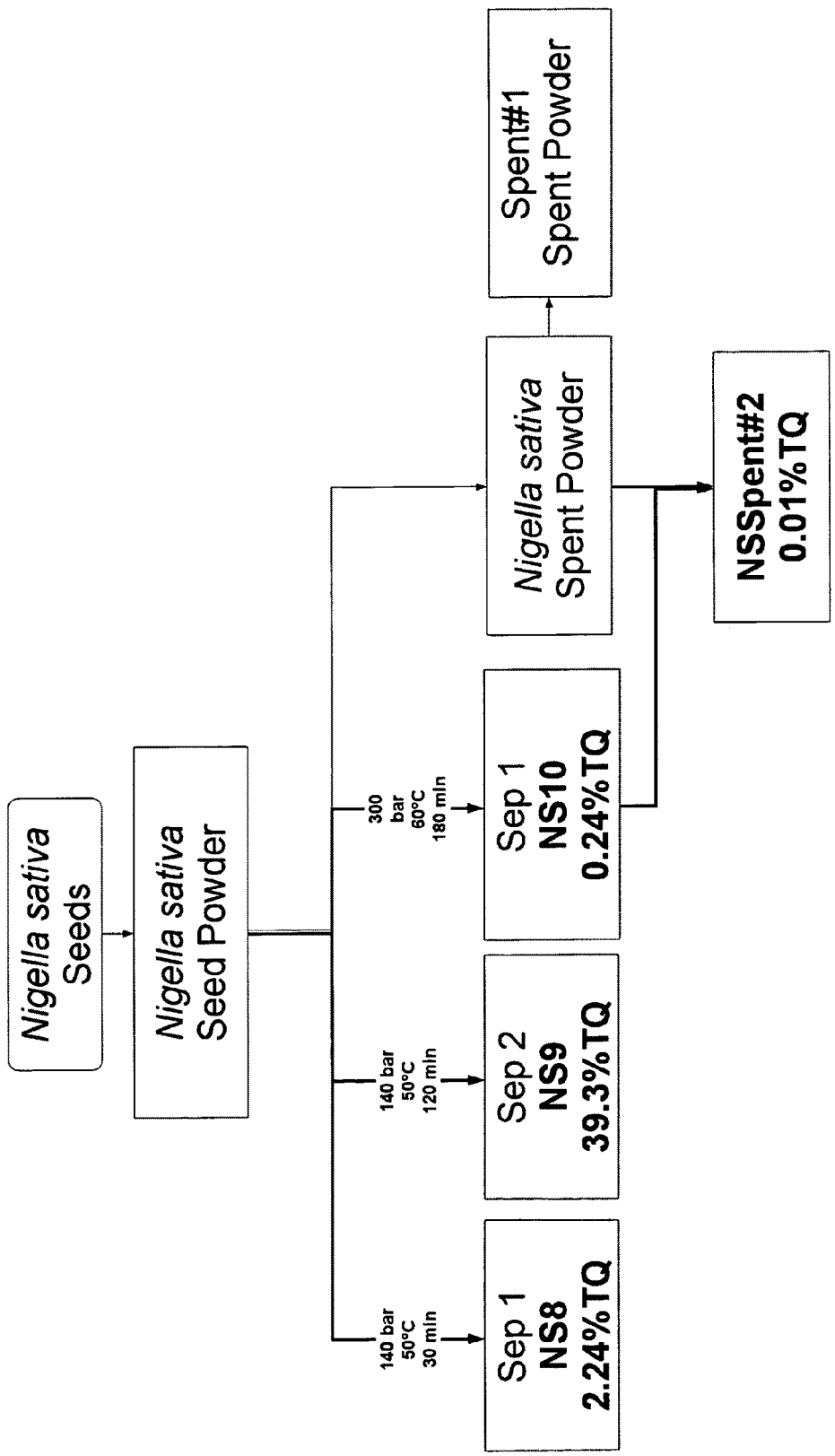
FIG. 4 describes the unique fractions obtained under various conditions of supercritical $CO_2$ extraction of *N. sativa* powdered seeds.

Finally, a fourth, novel TQ-containing composition Spent#2 was created by combining fractions NS10 with the extracted (Spent#1) *N. sativa* powdered seed in a ratio of 24:1 (extracted seed powder:NS10). The resulting TQ concentration of this sample was 0.01%. The extraction protocol is represented schematically in FIG. 4.

Relative to the research-scale process and prior art, the commercial-scale, supercritical $CO_2$ extraction process demonstrated remarkable efficiency in extraction of TQ in the production of NS9. Unexpectedly, using a low-pressure, single-step extraction process, the commercial-scale extraction produced a fraction containing nearly 40% TQ (NS9). This dramatic increase in TQ for extract NS9 was apparently due to reduced TQ recovery from the earlier fraction NS8 and resulted in lower TQ in the subsequent NS10 fraction.

TABLE 2

Contrasting Thymoquinone Content of Supercritical Carbon Dioxide Extraction of Research Quantities (100 g) and Commercial-Scale Quantities (100 kg) of *N. sativa* Seed Powder Under Various Extraction Conditions of Pressure, Temperature and Time

| Sample | Process conditions | | | Thymoquinone Content (% w/w) | |
|---|---|---|---|---|---|
| | Pressure (Bar) | Temperature (° C.) | Time (min) | 100 g Extracted | 100 kg Extracted |
| NS8 (1/2/3/4) | 140 | 50 | 30 | 5.47 | 2.24 |
| NS9 (5) | 140 | 60 | 120 | 2.95 | 39.3 |
| NS10 (6/7) | 300 | 60 | 180 | 1.29 | 0.24 |

As commercial-scaled supercritical $CO_2$ extraction of *N. sativa* has never before been attempted, these fractions were considered novel and placed into a screening program to assess potential health benefits. Results of the screening of these novel extracts are presented in the following Examples.

Example 2

Free Radical Scavenging Activity of Supercritical Carbon Dioxide Extract NS9 of *Nigella sativa* is Greater than Thymoquinone Objective—The objective of this experiment was to compare the antioxidant (free radical scavenging) activity of the four NS fractions obtained by supercritical $CO_2$ extraction of *N. sativa* powdered seeds in Example 1 with the pure TQ marker compound.

Chemicals—TQ, 2,2-diphenyl-1-picrylhydrazyl and all other compounds used in this example were purchased from Sigma (St. Louis, Mo.) and were of the highest purity commercially available. The four *N. sativa* samples used in this study were those commercial-scale extracts described in Example 1.

Methodology—Antioxidant activity was determined utilizing 2,2-diphenyl-1-picrylhydrazyl (DPPH), which is a stable radical. The odd electron in the DPPH free radical gives a strong absorption maximum at 550 nm and is purple in color. The color turns from purple to yellow as the molar absorption of the DPPH radical at 550 nm is reduced when the odd electron of DPPH radical becomes paired with hydrogen from a free radical scavenging antioxidant to form the reduced DPPH-H. The test samples were dissolved in methanol containing 1% dimethyl sulfoxide and added to microtiter wells in 100 µL aliquots to 100 µL of a 100 µM DPPH solution in methanol. Readings were taken at 10, 30 and 60 minutes following the addition of the test material. Percent inhibition of the DPPH radical by the test material was computed relative to the inhibition of the DPPH radical by the vitamin E analog trolox and tabulated as µmol trolox/g test material.

Results—Only NS9 of the four TQ-containing supercritical extracts exhibited antioxidant activity in the DPPH assay (Table 3). The antioxidant activity exhibited by NS9, however, was 3.3-times the activity seen with pure TQ. When compared to the literature, this result underscores the difference between supercritical $CO_2$ essential oil extracts of *N. sativa* and those resulting from use of organic solvents or steam distillation. For example, the DPPH-reducing activity of the essential oil fraction of *N. sativa*, produced by light petroleum Soxhlet extraction followed by steam distillation and containing 48% TQ, was reported to be less than one-half that of the TQ standard. When adjusted for TQ content, however, it appeared that all of the antioxidant activity of the essential oil fraction was due to TQ. (Burits, M.; Bucar, F., Antioxidant activity of *Nigella sativa* essential oil. *Phytother Res* 2000, 14 (5), 323-8). Thus, although the TQ content of the cited published study was 48% compared to 39% for fraction NS9, the antioxidant activity of the supercritical $CO_2$ *N. sativa* extract NS9 was quantitatively superior to the both the organic extract and TQ. This example demonstrates that the chemical behavior of *N. sativa* seed extracts is largely a function of extraction conditions such as solvent, temperature and time and independent of TQ concentration.

TABLE 3

Antioxidant Activity of Supercritical Carbon Dioxide Fractions of *N. sativa* Seeds Relative to Thymoquinone and Petroleum Extracted Fraction of *N sativa* Seeds

| Test Material | Thymoquinone Content [%] | DPPH Reducing Activity(1) [µmol Trolox/g TQ] |
|---|---|---|
| Thymoquinone (Sigma) | 100 | 45.2 |
| Essential Oil (Petroleum Ext)[2] | 48 | 43.2 |
| NS8 | 2.24 | No activity up to 1000 µg/mL |
| NS9 | 39.3 | 148 |
| NS10 | 0.24 | No activity up to 1000 µg/mL |
| Spent#1 | 0.00 | No activity up to 1000 µg/mL |
| NSSpent#2 | 0.010 | No activity up to 1000 µg/mL |

(1)Computed on basis of TQ content.
[2]Burits, M.; Bucar, F., Antioxidant activity of *Nigella sativa* essential oil. Phytother Res 2000, 14 (5), 323-8.

Conclusion—A supercritical $CO_2$ essential oil extract of *N. sativa* collected at 140 bar, 60° C. and 120 minutes and containing about 39% TQ possessed over three times the free radical savaging activity of TQ alone. As the prior art teaches that the TQ content of the essential oil fraction of *N. sativa* solely contributes to the antioxidant activity, unexpectedly, the unique combination of compounds extracted from *N. sativa* in NS 9 behaves synergistically to greatly exceed the antioxidant activity of the putative active component TQ.

Example 3

Inhibition of Prostate Specific Antigen Secretion from LNCaP Prostate Cells by Supercritical Carbon Dioxide Extracts of *Nigella sativa* Differs Qualitatively and Quantitatively from Thymoquinone Objective—While the effects of TQ and various extracts of *N. sativa* have shown cytotoxicity to a number of tumor cell lines, no studies have been done on the effect of TQ-containing extracts of *N. sativa* on the secretion of prostate specific antigen (PSA), a marker for prostate hyperplasia as well as cancer. While PSA is present in small quantities in the serum of normal men, it is often elevated in the presence of nonproliverative as well as neoplastic prostate disorders. Examples of noncancerous or nonproliverative prostate disorders exhibiting elevated PSA are benign prostate hyperplasia and infections of the prostate. The objective of this experiment was to determine whether commercial-scale, supercritical fluid $CO_2$ extracts of *N. sativa* containing TQ would affect prostate specific antigen secretion from non-proliferating prostate cells in a manner similar to TQ alone.

Chemicals—PSA was quantified from the cell culture supernatant fluid using the Quantikine Human KLK3/PSA Immunoassay kit (R&D Systems, Inc., Minnaepolis, Minn.). All other materials used in this example were purchased from Sigma (St. Louis, Mo.) or otherwise noted and were of the highest purity commercially available. The *N. sativa* samples used in this study were those commercial-scale extracts described in Example 1.

Cell culture and treatment—The LNCaP prostate cell line, which produces PSA, was used to study the effects of commercial-scale *N. sativa* scale extracts of Example 1 and pure TQ on the secretion of PSA. LNCaP cells were purchased from the American Type Culture Collection (ATCC, Manassas, Va.) and sub-cultured according to instructions supplied by ATCC. Prior to experiments, cells were cultured in DMEM containing 10% FBS-HI added 50 units penicillin/ml and 50 µg streptomycin/ml, and maintained in log phase prior to experimental setup. Cells were grown in a 5% $CO_2$ humidified incubator at 37° C. Components of medium included: (1) 10% FBS/DMEM (Fetal Bovine Serum/Dulbecco's Modified Eagle's Medium) containing 4.5 g glucose/L; (2) 50 U/ml penicillin; and (3) 50 µg/ml streptomycin. Growth medium was made by adding 50 ml of heat inactivated FBS and 5 ml of penicillin/streptomycin to 500 ml DMEM. This medium was stored at 4° C. Before use, the medium was warmed to 37° C. in a water bath.

LNCaP cells were seeded at an initial density of $6 \times 10^4$ cells/$cm^2$ in 96-well plates. For two days, the cells were allowed grow to reach confluence. On day three post seeding, cells were treated with TQ, NS8, NS9, NS10, Spent#1, and NSSpent#2 at the concentrations listed in FIGS. 5, 6 and 7. Twenty-four hours later, the supernatant media were sampled and assayed for PSA.

TABLE 4

Summary of Effects on Prostate Specific Antigen Secretion by LNCaP Prostate Cells by Supercritical Extracts of *Nigella sativa* Seeds and Pure Thymoquinone

| Test Material | Effect on PSA Secretion over 24 Hours |
|---|---|
| Thymoquinone (Sigma) | Decreased PSA at 5 and 10 µg/mL, dramatic increase in PSA secretion at 50 and 100 µg/mL. |
| NS8 | Increased PSA secretion at all doses, but decreased with increasing NS8. |
| NS9 | Dose-related decrease in PSA from 5 to 100 µg/mL. |
| NS10 | Dose-related increase in PSA from 5 to 100 µg/mL. |
| Spent#1 | Increase in PSA secretion at both doses tested 250 and 500 µg/mL. |
| NSSpent#2 | Decrease in PSA secretion at both doses tested 250 and 500 µg/mL. |

Figure 5:
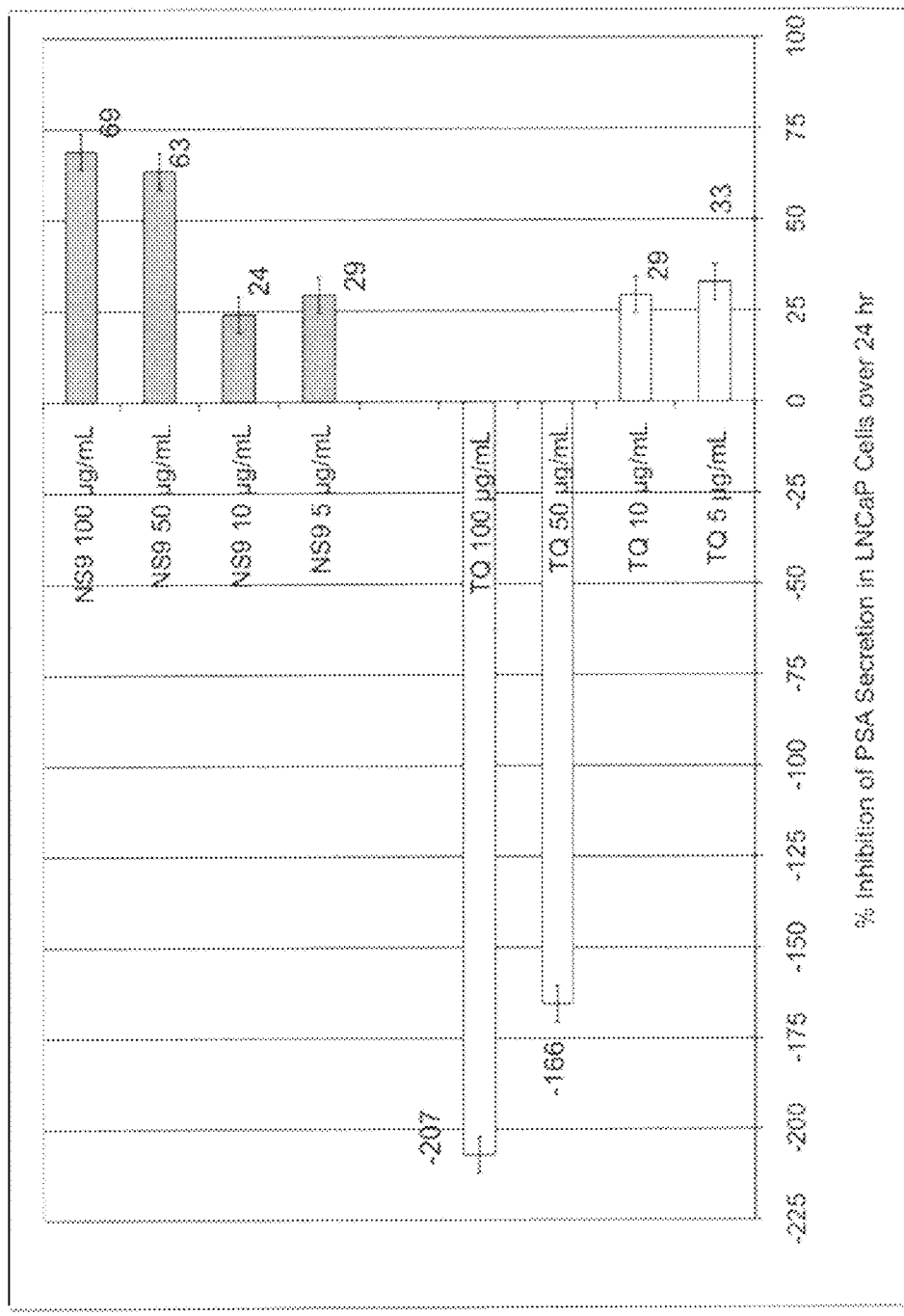
FIG. 5 depicts the relative inhibition and stimulation, respectively, of prostate specific antigen by *N. sativa* supercritical fraction NS9 and pure TQ adjusted for viable LNCaP prostate cells.
Figure 6:
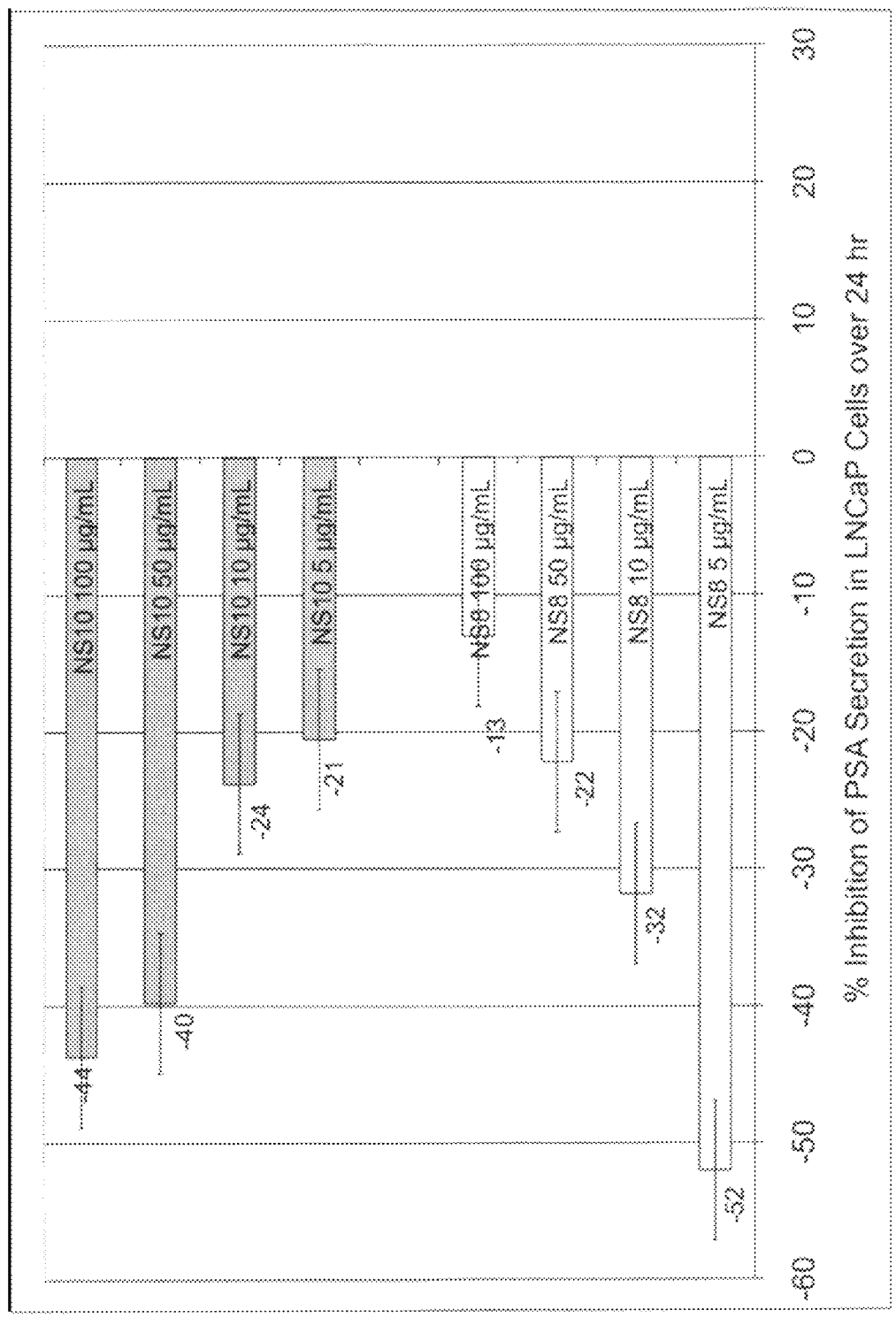
FIG. 6 depicts the dose-related decrease and dose-related increase, respectively, of prostate specific antigen by *N. sativa* supercritical fractions NS8 and NS9 adjusted for viable LNCaP cells.
Figure 7:
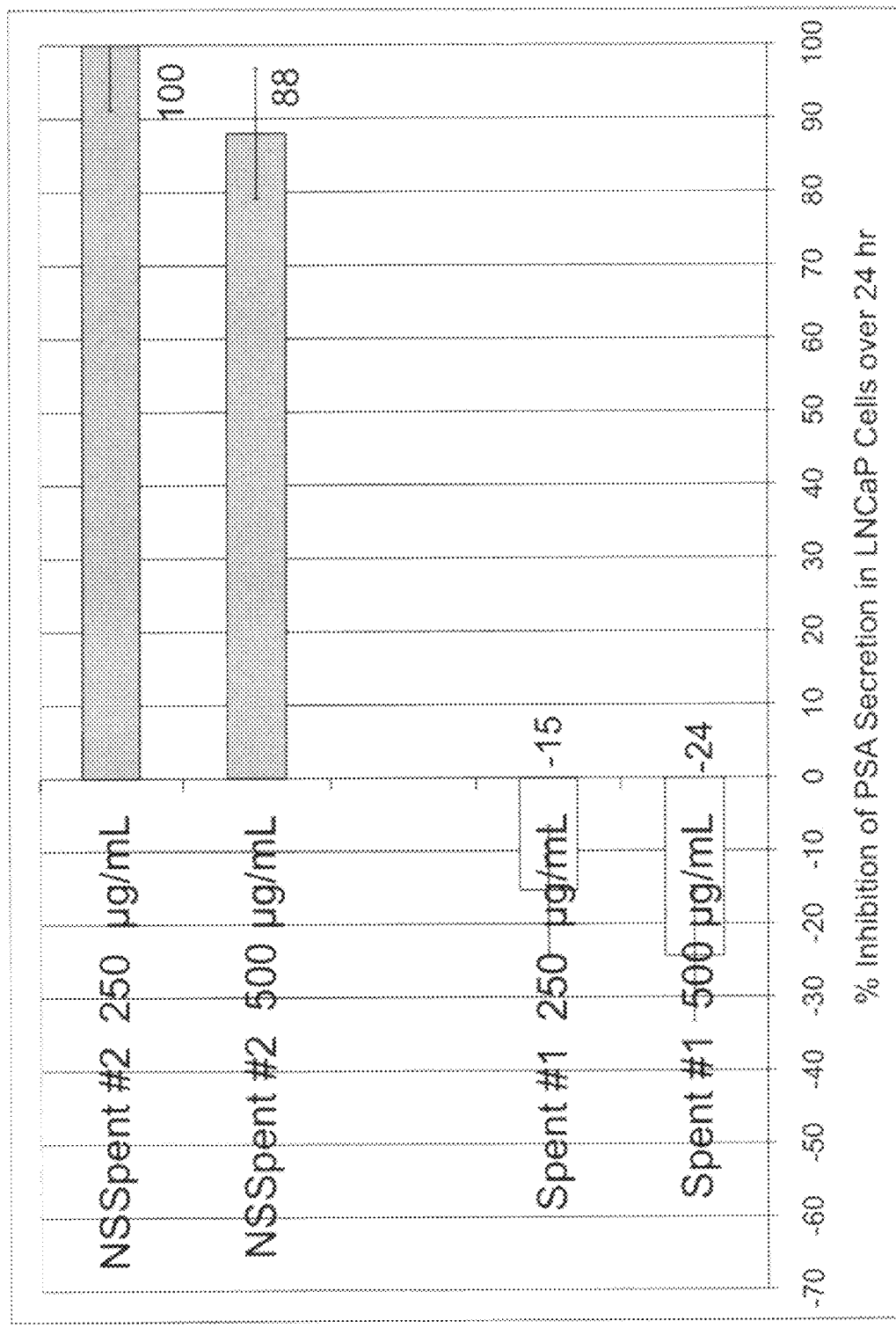
FIG. 7 depicts the relative inhibition and stimulation, respectively, of prostate specific antigen by *N. sativa* supercritical fraction NS/Spent#2 and Spent#1 adjusted for viable LNCaP cells.

Results—FIGS. 5, 6 and 7 depict the pair-wise contrasts, respectively, of TQ vs NS9, NS8 vs NS10, and Spent#1 vs NSSpent#2. Unexpectedly, TQ did not exhibit a linear dose-response curve and decreased PSA only at the two lowest doses tested while dramatically increasing PSA secretion at the highest doses, 166 and 207%. The response of NS9 differed qualitatively from that of TQ alone. NS9 produced a linear dose-related decrease in PSA over all four concentrations (FIG. 5). NS8 and NS10 differed in their effect on PSA secretion from both TQ and NS9. NS8 increased PSA at all doses, but this effect decreased with increasing NS8 concentration (FIG. 6). Conversely, NS10 increased PSA at all doses in a direct dose-response relationship. Finally, while Spent#1 increased PSA at both 250 and 500 µg/mL, NSSpent#2 nearly totally decreased PSA secretion at both of these concentrations.

A summary of the various effect of *N. sativa* supercritical $CO_2$ extracts on PSA secretion is presented in Table 4. It is clear from this summary that these extracts produce novel effects on PSA secretion from prostate cells implying differences in composition and biological activity not anticipated in the prior art.

Example 4

Select Commercial Supercritical Fluid Extracts of *Nigella sativa* are Potent Uncouplers of Mitochondrial Membrane Potential in 3T3-L1 Adipocytes Objective—The objective of this experiment was to determine whether commercial-scale, supercritical $CO_2$ extracts of *N. sativa* powdered seeds produced in Example 1 directly reduce mitochondria membrane potential in 3T3-L1 adipocytes compared to pure TQ or DNP.

The model—3T3-L1 murine fibroblast are routinely used to study the potential effects of compounds on white adipose tissue in vitro. This cell line allows investigation of stimuli and mechanisms that regulate inflammatory mediators of cytokine secretion of the adipocyte. As preadipocytes, 3T3-L1 cells have a fibroblastic appearance. They replicate in culture until they form a confluent monolayer, after which cell-cell contact triggers $G_0/G_1$ growth arrest. Terminal differentiation of 3T3-L1 cells to adipocytes depends on proliferation of both pre- and post-confluent preadipocytes. Subsequent stimulation with 3-isobutyl-1-methylxanthane, dexamethasone, and high does of insulin (MDI) for two days prompts these cells to undergo post-confluent mitotic clonal expansion, exit the cell cycle, and begin to express adipocyte-specific genes. Approximately five days after induction of differentiation, more than 90% of the cells display the characteristic lipid-filled adipocyte phenotype. At this stage of differentiation, response to mitochondrial uncouplers such as DNP may be assessed.

Chemicals—2,4-Dinitrophenol and all other chemicals used in this example were purchased from Sigma (St. Louis, Mo.) or otherwise noted and were of the highest purity commercially available. The *N. sativa* commercial-scale extracts used in this study were those described in Example 1.

Cell culture and Treatment—The murine fibroblast cell line 3T3-L1 was purchased from the American Type Culture Collection (Manassas, Va.) and sub-cultured according to instructions from the supplier. Prior to experiments, cells were cultured in DMEM containing 10% FBS-HI added 50 units penicillin/ml and 50 µg streptomycin/ml, and maintained in log phase prior to experimental setup. Cells were grown in a 5% $CO_2$ humidified incubator at 37° C. Components of the pre-confluent medium included: (1) 10% FBS/DMEM (Fetal Bovine Serum/Dulbecco's Modified Eagle's Medium) containing 4.5 g glucose/L; (2) 50 U/ml penicillin; and (3) 50 µg/ml streptomycin. Growth medium was made by adding 50 ml of heat inactivated FBS and 5 ml of penicillin/streptomycin to 500 ml DMEM. This medium was stored at 4° C. Before use, the medium was warmed to 37° C. in a water bath.

3T3-T1 cells were seeded at an initial density of $6 \times 10^4$ cells/$cm^2$ in 96-well plates. For two days, the cells were allowed grow to reach confluence. Following confluence, the cells were forced to differentiate into adipocytes by the addition of differentiation medium; this medium consisted of (1) 10% FBS/DMEM (high glucose); (2) 0.5 mM methylisobutylxanthine; (3) 0.5 µM dexamethasone and (4) 10 µg/ml insulin (MDI medium). After three days, the medium was changed to post-differentiation medium consisting of 10 µg/ml insulin in 10% FBS/DMEM.

Treatment with 2,4-Dinitrophenol and Test Material—On Day 6 post differentiation, DNP or test materials TQ, NS8, NS9, or NS10 were dissolved in DMSO and added to the culture medium to achieve concentrations of 500 μM for DNP and 25 μg/mL for the test materials each in eight wells of a single column 60 min at 37° C. JC-1 was then added to the test and negative control columns in 10 μL DMSO to achieve a final concentration of 5 μM and allowed to incubate at 37° C. for an additional 30 min. A DMSO and solvent plus JC-1 control were run concurrently with each experiment. A Packard Fluorocount spectrofluorometer (Model #BF10000, Meridan, Conn.) set at 560 nm excitation and 590 nm emission was used for quantification of aggregate fluorescence and at 485 nm excitation/530 emission for monomer fluorescence.

Measuring mitochondrial membrane potential changes ($\Delta\Psi m$)—JC-1 (Sigma, St. Louis, Mo.) has advantages over other cationic dyes in that it can selectively enter into mitochondria and reversibly change color from green to red as the membrane potential increases. In healthy cells with high mitochondrial membrane potential ($\Delta\Psi m$), JC-1 spontaneously forms complexes known as J-aggregates with intense red fluorescence. On the other hand, in cells with low $\Delta\Psi m$, JC-1 remains in the monomeric form exhibiting only green fluorescence. The changes in $\Delta\Psi m$ by different forms of JC-1 as either green or red fluorescence are both quantified by a fluorescence plate reader with appropriate filter sets.

Calculation of relative decrease in mitochondrial membrane potential—Aggregate and monomer fluorescence was computed for the 500 μM DNP positive control as well as the test materials TQS, NS8, NS9 or NS10 relative to JC-1 negative controls. The ratio of the monomer to aggregate relative fluorescence was then determined as a measure of relative decrease in $\Delta\Psi m$. For statistical comparisons, 95% confidence intervals were computed (Excel, Microsoft, Redman, Wash.) and graphed (FIG. 8) with the mean relative monomer/aggregate ratios. By utilizing the 95% confidence intervals, the probability of a type I error was set at the nominal 5% level.

Figure 8:
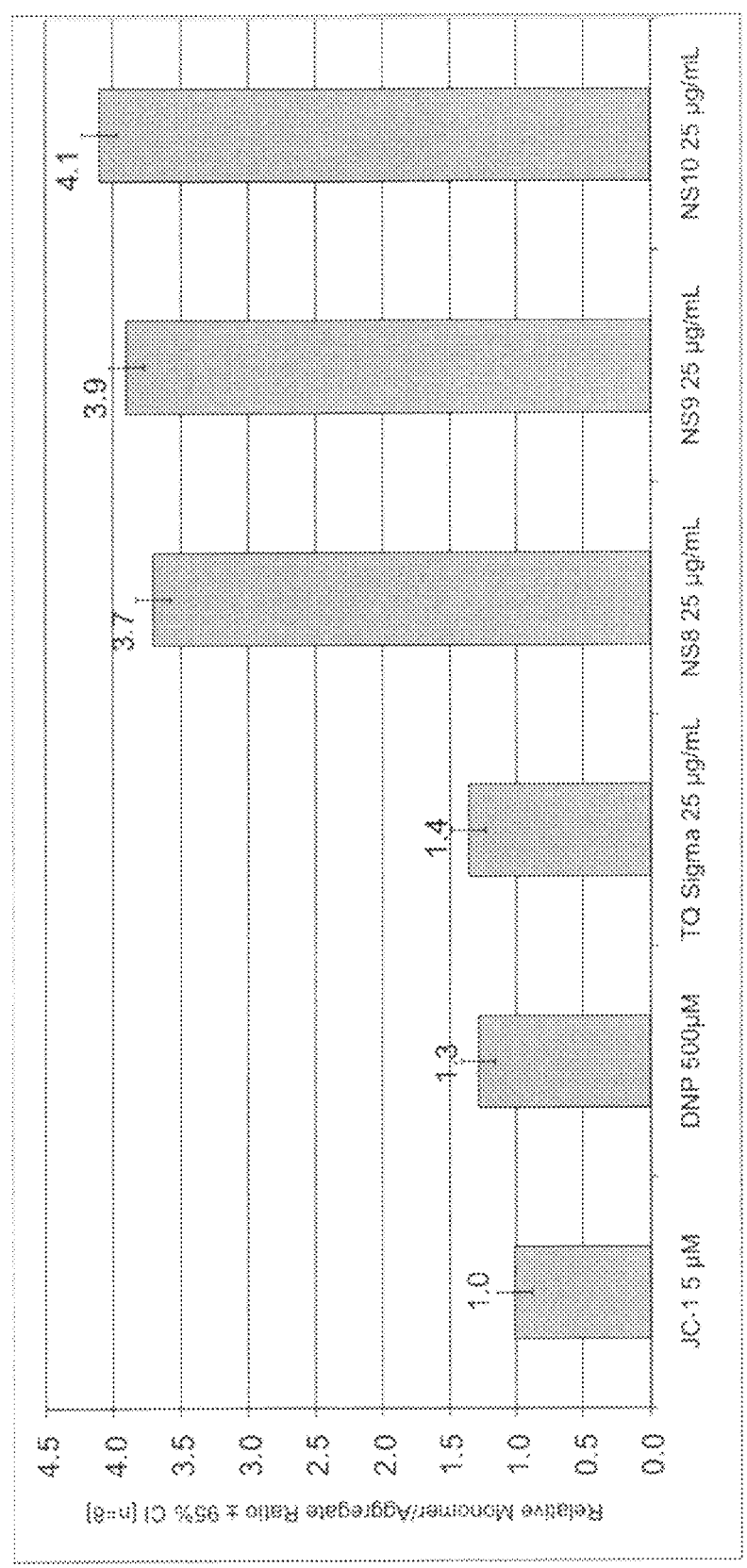
FIG. 8 depicts the relative FC-1 monomer/aggregate fluorescence in 3T3-L1 adipocytes treated with 500 µM dinitrophenol or test materials TQ, NS8, NS9 or NS10 dosed at 25 µg/mL.

Results—The positive control DNP at 500 μM decreased in $\Delta\Psi m$ in 3T3-L1 adipocytes to a similar extent as 25 μg/mL pure TQ, approximately 30 to 40% (FIG. 8). The *N. sativa* commercial-scale extracts NS8, NS9 and NS10, however, decreased mitochondrial membrane potential 3.7- to 4.1-fold relative to solvent controls. This example further demonstrates that the commercial-scale, supercritical $CO_2$ extracts of *N. sativa* possess biological activity unexplained by TQ content alone.

Example 5

Select Supercritical Fluid Extracts of *Nigella sativa* Inhibit Inflammation-Stimulated Nitric Oxide Biosynthesis in Adipocytes and Myocytes Objective—The objective of this experiment was to determine whether the commercial-scale, supercritical $CO_2$ extracts of *N. sativa* seeds obtained in Example 1 reduce inflammation-induced NO secretion in adipocytes and myocytes as effectively as TQ alone.

The model—The murine 3T3-L1 preadipocyte and murine C2C12 premyocyte models were used in this Example. This model was selected to serve as the surrogate for adipocytes and myocytes that are exposed to a variety of the inflammatory stimuli of invading bacteria, modeled by lipopolysaccharide (LPS), as well as the counter-inflammatory responses of infiltrating macrophage, modeled by interferon gamma (IFγ) and tumor necrosis factor alpha (TNFα). Additionally alterations in NO levels have been demonstrated in pathologic conditions in humans such as obesity, diabetes, hypertension, osteoarthritis, osteoporosis, and interstitial cystitis.

Chemicals—Heat-inactivated fetal bovine serum (HIFBS), penicillin and streptomycin solution, and Dulbecco's Modification of Eagle's Medium (DMEM) were purchased from Mediatech (Herndon, Va.). 2-N-7-(nitrobenz-2-oxa-1,3-diazol-4-yl)amino-2-deoxy-d-glucose (2-NBDG) and N-methyl-4-hydrazino-7-nitrobenzofurazan (NBDM) were obtained from Invitrogen (Carlsbad, Calif.). TQ, bacterial lipopolysaccharide (LPS), murine TNFα and Interferon-γ and all standard chemicals, unless noted, were obtained from Sigma (St Louis, Mo.) and were of the highest purity commercially available.

Cell culture and treatment—The murine fibroblast cell line 3T3-L1 was purchased from the American Type Culture Collection (Manassas, Va.) and sub-cultured according to instructions from the supplier. Prior to experiments, cells were cultured in DMEM containing 10% FBS-HI added 50 units penicillin/ml and 50 μg streptomycin/ml, and maintained in log phase prior to experimental setup. Cells were grown in a 5% $CO_2$ humidified incubator at 37° C. Components of the pre-confluent medium included: (1) 10% FBS/DMEM (Fetal Bovine Serum/Dulbecco's Modified Eagle's Medium) containing 4.5 g glucose/L; (2) 50 U/ml penicillin; and (3) 50 μg/ml streptomycin. Growth medium was made by adding 50 ml of heat inactivated FBS and 5 ml of penicillin/streptomycin to 500 ml DMEM. This medium was stored at 4° C. Before use, the medium was warmed to 37° C. in a water bath.

3T3-T1 cells were seeded at an initial density of $6\times10^4$ cells/$cm^2$ in 24-well plates. For two days, the cells were allowed grow to reach confluence. Following confluence, the cells were forced to differentiate into adipocytes by the addition of differentiation medium; this medium consisted of (1) 10% FBS/DMEM (high glucose); (2) 0.5 mM methylisobutylxanthine; (3) 0.5 μM dexamethasone and (4) 10 μg/ml insulin (MDI medium). After three days, the medium was changed to post-differentiation medium consisting of 10 μg/ml insulin in 10% FBS/DMEM.

For assessing the effects of the *N. sativa* extracts on cytokine-stimulated NO-production in 3T3-L1 adipoctyes, D6 adipoctyes were treated with 50, 10, 5, or 1 μg TQ or *N. sativa* extract/mL for 1 hour and then stimulated with a cytokine mixture containing 1 μg LPS/mL, 50 ng TNFα/mL and 100 U IFγ/mL (LTI) for 20 hours. L-$N^G$-Nitroarginine methyl ester (L-NAME) at 200 μM (47 μg/mL) was used as the positive control and 0.1% DMSO for the negative control.

Mouse C2C12 myoblasts (American Type Culture Collection, Manassas, Va.) were maintained in Dulbecco's modified Eagle's medium (DMEM) supplemented with 10% fetal calf serum (FCS), 50 units/ml penicillin and 50 μg/ml streptomycin. As cells reached confluence, the medium was switched to the differentiation medium containing DMEM and 2% horse serum. Medium was changed every other day. After 4 additional days, the differentiated C2C12 cells had fused into myotubes, which were then treated in serum-free DMEM with either vehicle alone (0.1% DMSO), or 50, 10, 5, or 1 μg TQ or *N. sativa* extract/mL for 1 hour and then stimulated with a cytokine mixture containing 1 μg LPS/mL, 50 ng TNFα/mL and 100 U IFγ/mL (LTI) for 20 hours. At the end of the treatment period, media were sampled for determination of NO.

Nitric oxide determination—NBD methylhydrazine (NBDM, N-methyl-4-hydrazino-7-nitrobenzofurazan) was used to detect N-methyl-4-amino-7-nitrobenzofuazan, the fluorescent product of the NBDM reagent with nitrite (Buldt A, Karst U. Determination of nitrite in waters by microplate fluorescence spectroscopy and HPLC with fluorescence detection. *Anal Chem*. Aug. 1 1999; 71(15):3003-3007). In a separate, black-walled, 96-well, microtiter plate, a 7 µL aliquot of a $4.8 \times 10^{-4}$ mol NBDM/L solution was added to 200 µL of the supernatant media followed by the addition of 15 µL of concentrated phosphoric acid. After a reaction time of 30 minutes at ambient temperature, the fluorescence was read with 485 nm excitation filter and a 530 nm emission filter in a Packard Fluorocount spectrofluorometer (Model #BF10000, Meridan, Conn.). Fluoresence was linear in the range of $3.59 \times 10^{-7}$ to $1.44 \times 10^{-5}$ mol nitrite/L. The standard deviation was 3.5 percent for $1.44 \times 10^{-6}$ mol nitrite/L. Experiments were performed a minimum of three times with eight replicates per dose, capturing the median inhibitory concentration ($IC_{50}$) when possible.

Calculations—The median inhibitory concentrations ($IC_{50}$) and 95% confidence interval were calculated using CalcuSyn (BIOSOFT, Ferguson, Mo.). This statistical package performs multiple drug dose-effect calculations using the Median Effect methods described by Chou and Talalay [Chou T C, Talalay P. Quantitative analysis of dose-effect relationships: the combined effects of multiple drugs or enzyme inhibitors. *Adv Enzyme Regul*. 1984; 22:27-55].

TABLE 5

Median Inhibitory Concentrations of Three Supercritical Fluid Extracts of *N. sativa* and Thymoquinone for iNOS-mediated NO Biosynthesis in Adipocytes and Myocytes

| Test Sample | 3T3-L Adipocytes* [µg/mL] | C2C12 Myocytes* [µg/mL] |
|---|---|---|
| TQS (100% TQ) | 1.9 (1.4-2.7) | 1.9 (1.0-3.4) |
| NS8 (2.24% TQ) | 1.2† | 0.11† |
| NS9 (39.3% TQ) | 1.6 | 1.6 |
| NS10 (0.24% TQ) | 6.5† | 0.007† |
| NSSpent#2 | 0.92† | Not Tested |

*Value computed on the basis of TQ content.
†Significantly different (p < 0.05) from TQS.

Results—TQ alone was a potent inhibitor of iNOS-mediated NO production in both adipocytes and myocytes stimulated with the trivalent cytokine mixture and exhibited a median inhibitory concentrations of 1.9 µg TQ/mL in both cell types (Table 5). These results are consistent with published results for NO inhibition in the LPS-stimulated macrophages ($IC_{50}$=1.4-2.8 µg/mL). [El-Mahmoudy A, Matsuyama H, Borgan M A, et al. TQ suppresses expression of inducible nitric oxide synthase in rat macrophages. *Int Immunopharmacol*. October 2002; 2(11):1603-1611]. The four supercritical extracts of *N. sativa* tested in this example NS8, NS9, NS10 and NSSpent#2 were all also potent inhibitors of LTI-stimulated NO biosynthesis in 3T3-L1 adipocytes and C2C12 myocytes (NSSpent#2 not tested in myocytes). While NS8 and NS9 were equally potent to TQ alone computed on the basis of TQ content, NSSpent#2 was more potent and NS10 less potent than TQ in adipocytes. Conversely, NS10 was more potent than TQ in the C2C12 myocytes. Consistent with its response in 3T3-L1 adipocytes NS8 was equally as potent as TQ in the C2C 12 myocytes.

These unexpected results serve to demonstrate the superior NO inhibitory potency of specific supercritical extracts of *N. sativa* over TQ alone.

Thus, the inhibitory effects of *N. sativa* supercritical fluid extracts in this example demonstrate a novel result encompassing multiple receptor signaling pathways in adipocytes and myocytes. Such a finding has thus far not been reported in the prior art.

Example 6

Select Supercritical Fluid Extracts of *Nigella sativa* Increase Lypolysis in 3T3-L1 Adipocytes and C2C12 Myocytes Objective—The objective of this experiment was to determine whether the supercritical fluid $CO_2$ extracts of *N. sativa* obtained in Example 1 induce lipolysis in adipocytes or myocytes.

Chemicals—All chemicals used in this example were purchased from Sigma (St. Louis, Mo.) or otherwise noted and were of the highest purity commercially available. The *N. sativa* samples used in this study were those described in Example 1.

Figure 9:
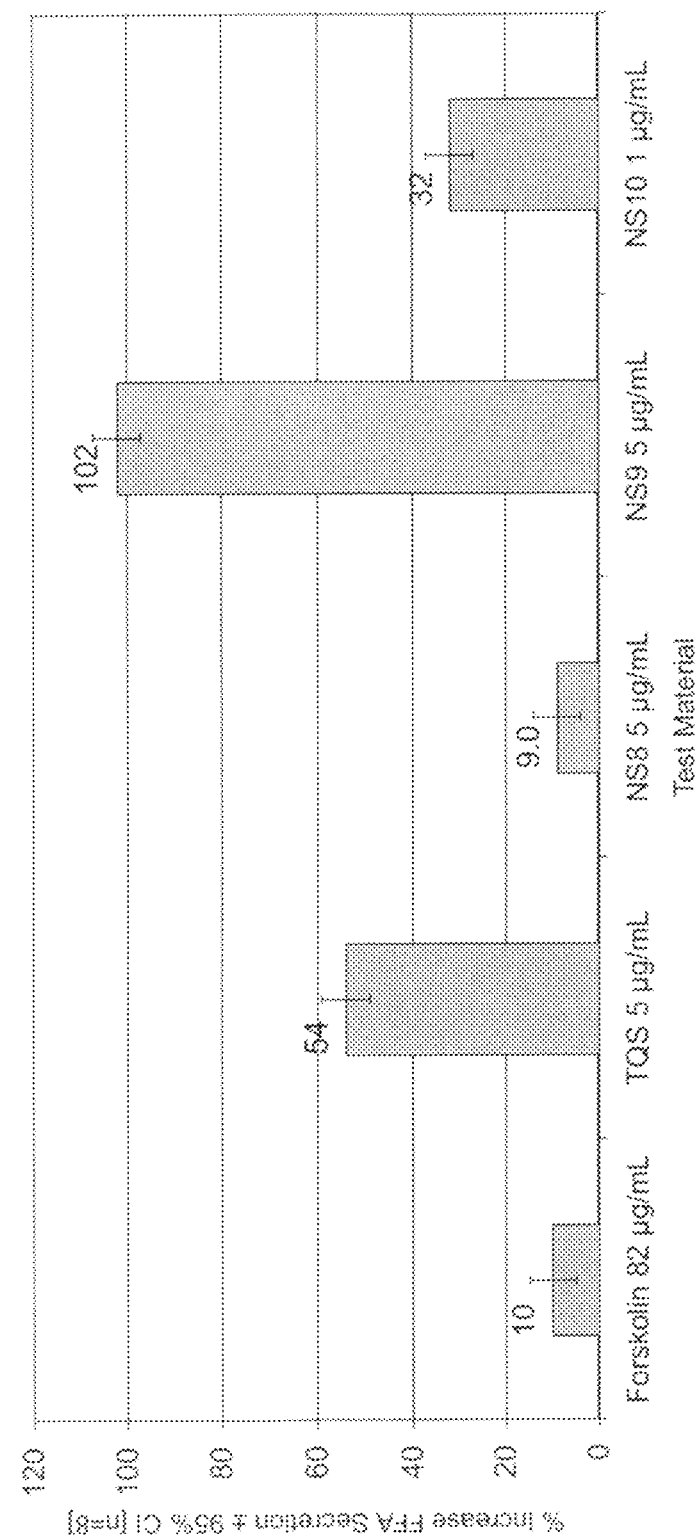
FIG. 9 depicts the relative free fatty acid release from 3T3-L1 adipoctyes treated with 82 µg/mL forskolin or test materials TQ, NS8, NS9, or NS10 dosed at 5 µg/mL.

Cell culture and treatment—Culture and treatment of 3T3-L1 adipocytes and C2C12 myocytes was as described in Example 5. Concentrations of the forskolin positive control and test materials are listed in FIG. 9 for adipocytes and FIG. 10 for myocytes.

Glycerol assay—Free fatty acid release from 3T3-L1 adipocytes or C2C12 myocytes was quantified by measuring glycerol secretion into the medium. Glycerol was measured spectrophotometrically using the Free Glycerol Determination Kit (F6428, Sigma) and an EL 312e Microplate BIO-KINETICS spectrophotometer (BioTek, Winooski, Vt.).

Data analysis—Glycerol release from adipocytes and myocytes was expressed, respectively, as the percent increase in free fatty acid secretion (FIG. 9) and relative glycerol content (glycerol index FIG. 10) ±95% confidence intervals of eight observations for one of three representative experiments.

Figure 10:
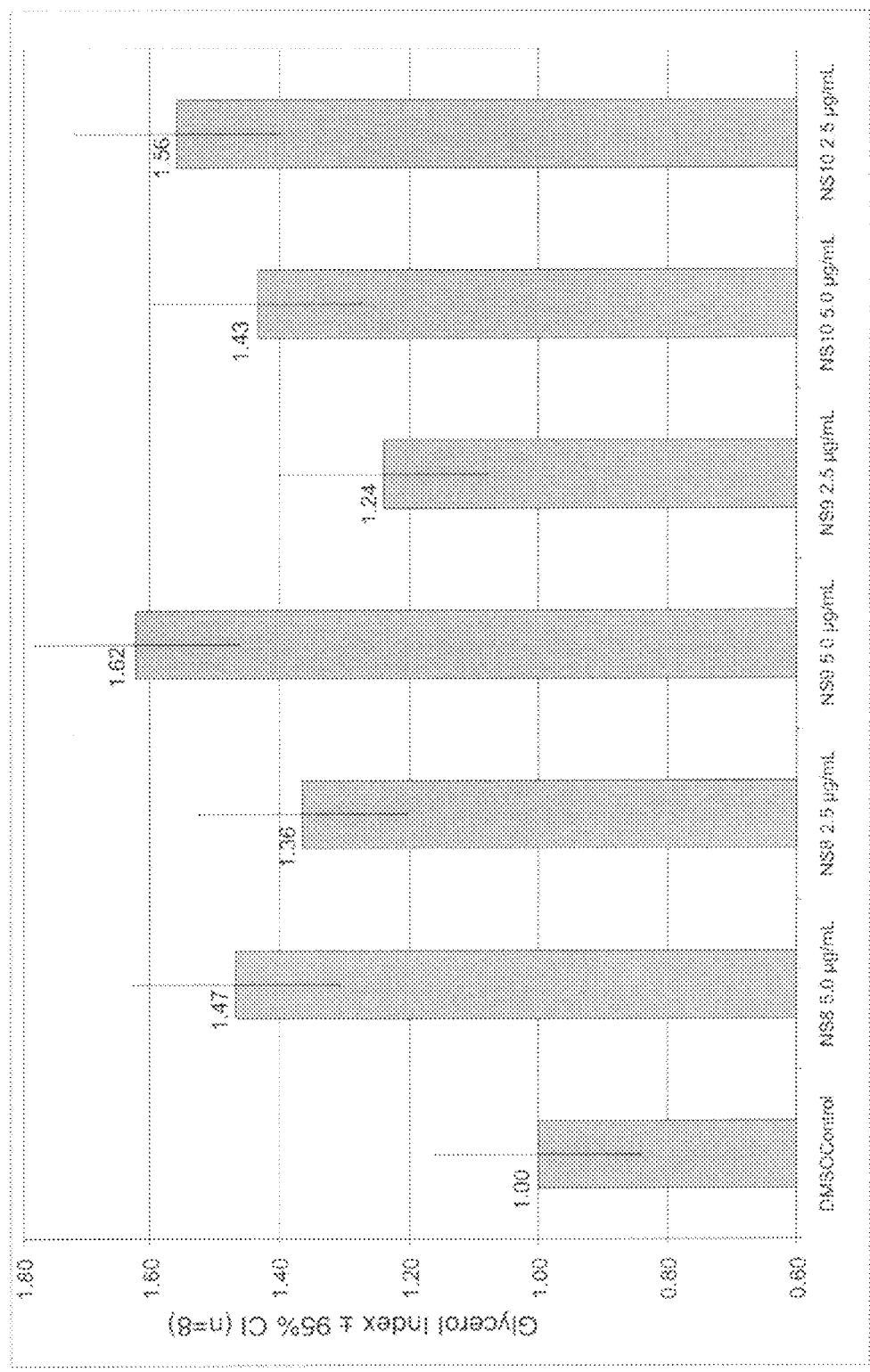
FIG. 10 depicts the relative free fatty acid release from C2C12 myocytes treated with materials NS8, NS9, or NS10 dosed at 5 or 2.5 µg/mL.

Results—The forskolin positive control, TQ and all NS supercritical extracts induced free fatty acid release in adipocytes (FIG. 9) and myocytes (FIG. 10). Specifically, NS8 at 5 µg/mL induced similar free fatty acid secretion from 3T3-L1 adipocytes as 82 µg/mL of the positive control forskolin. NS9, exhibiting an increase in free fatty acid release of 102% in adipocytes, was twice as potent as TQS (Sigma) on a weight basis and 4.8-times as potent based on a TQ content of 39%.

Example 7

Select Supercritical Fluid Extracts of *Nigella sativa* Activate AMPK in Myocytes Objective—The objective of this experiment was to compare the effect of the AMP mimentic AICAR on AMPK activation in C2C12 myocytes with the commercial-scale supercritical $CO_2$ extracts of *N. sativa* produced in Example 1.

The Model—The C2C12 myocyte model as described in Example 5 was used in this example.

Chemicals—Penicillin, streptomycin, Dulbecco's modified Eagle's medium (DMEM) was from Mediatech (Herndon, Va.) and 10% FBS-HI (fetal bovine serum-heat inactivated) were obtained from Mediatech and Hyclone (Logan, Utah). The commercial supercritical $CO_2$ extracts of *N. sativa* produced in Example 1 were used as the test materials. Unless noted, all other standard reagents were purchased from Sigma (St. Louis, Mo.).

Cell culture—Mouse C2C12 myoblasts were obtained from American Type Culture Collection (Manassas, Va.), and were maintained in Dulbecco's modified Eagle's medium (DMEM) supplemented with 10% fetal bovine serum at 37° C. under a humidified atmosphere of 5% $CO_2$.

C2C12 cells were seeded at an initial density of $6 \times 10^4$ cells/$cm^2$ in 24-well plates. For two days, the cells were allowed grow to reach confluence. Following confluence, the cells were forced to differentiate into myocytes by culturing in DMEM supplemented with 2% horse serum for seven days.

Treatment—On Day 8 to 10 post differentiation, C2C12 myocytes were incubated in serum-free DMEM plus 0.5% BSA (bovine serum albumin) for three hours. Next, AICAR (Cell Signal, Danvers, Mass.) was dissolved in phosphate buffered saline (PBS) and added to the culture medium to achieve concentrations of 1 mM. Test materials NS8, NS9 and NS10 were added in DMSO to achieve a final concentration of 25 μg test material/mL and one percent DMSO. After 30 minutes at 37° C., cell lysates were prepared for determination of activated AMPK.

Measuring activated AMPKa—$pT^{172}$-AMPK was quantified using the Biosource AMPK Immunoassay Kit (Camarillo, Calif.) without modification. Protein content of the cell lysates was determined with the Active Motif fluorescent protein assay reagent (Carlsbad Calif., Hoefelschweiger, B. K., Duerkop, A., and Wolfbeis, O. S. Novel type of general protein assay using a chromogenic and fluorogenic amine-reactive probe. *Anal Biochem* 2005, 344, 122-9). A Packard Fluorocount spectrofluorometer (Model #BF 10000, Meridan, Conn.) was used for protein determination and a MEL312e BIO-KINETICS READER (Bio-Tek Instruments, Winooski, Vt.) was used for quantification of $pT^{172}$-AMPK.

Calculation of relative activation of AMPK—$pT^{172}$-AMPK was computed per mg lysate protein and then normalized to the dimethyl sulfoxide (DMSO) negative controls. For statistical comparisons, 95% confidence intervals were computed (Excel, Microsoft, Redman, Wash.).

Figure 11:
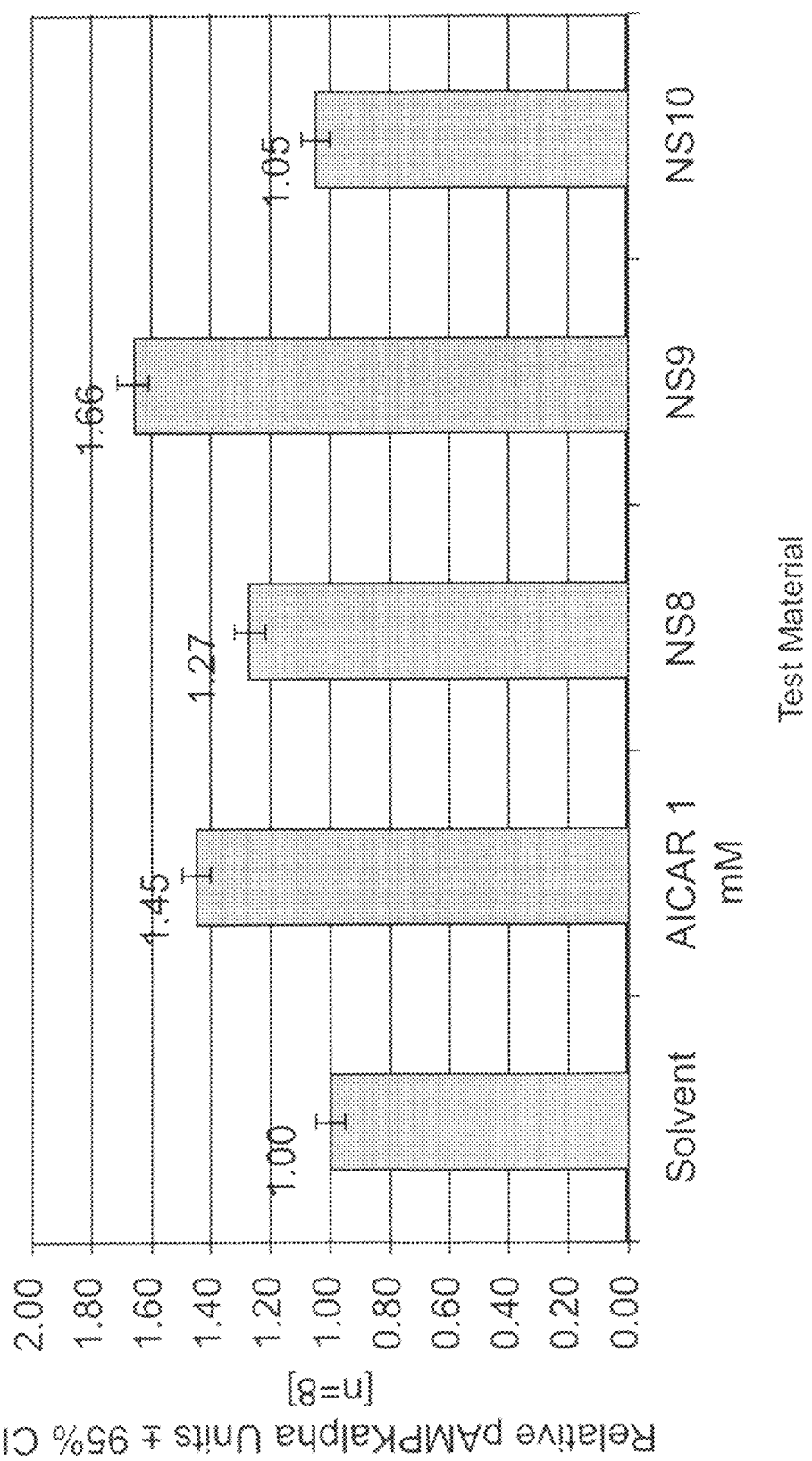
FIG. 11 depicts the relative increase in pAMPK in C2C12 myocytes treated with 1 mM AICAR and test materials NS8, NS9, or NS10 dosed at 25 µg/mL.

Results—Over ten independent assays, 1 mM AICAR increased $pT^{172}$-AMPK an average of 1.67-fold (95% CI=1.26-2.21) in C2C12 myocytes relative to the DMSO negative controls. In three independent assays, NS8 and NS9 fractions activated myocyte AMPK, while NS10 had no effect (FIG. 11). The AICAR positive control induced a 1.45-fold activation in assays run with *N. sativa* supercritical $CO_2$ extracts. In studies of direct comparisons, 25 μg NS9/mL was 14% more active (p<0.05) than 1 mM AICAR in activating AMPK.

Example 8

A Select Supercritical Fluid Extract of *Nigella sativa* Overcomes Adaptive Thermogenesis in Humans Resulting in Weight Loss Objective—The objective of this example was to assess the effect of supercritical $CO_2$ extract NS9 prepared using the commercial-scale process described in Example 1 on adaptive thermogenesis in an individual involved in a moderate aerobic exercise regimen that initially produced weight loss, but was no longer effective.

Test Material—Commercial scale NS9 as described in Example 1 containing 39% TQ was used as the test material.

Methods—A sixty-one year old male, who had been involved in a moderate, aerobic exercise program for a period of approximately one year, was directed to take two capsules of NS9 three times per day. The individual was further instructed not to change his exercise regimen or dietary habits. His body weight and blood pressure were recorded twice daily—within one hour of awakening in the morning and in the late afternoon for six months prior to the study and during the week of the study. The 99% confidence interval, computed from the previous six-month variation in day-to-day body weight for AM and PM weighing, was used to assess significant (p<0.01) decreases, respectively, in AM or PM body weight.

Figure 12:
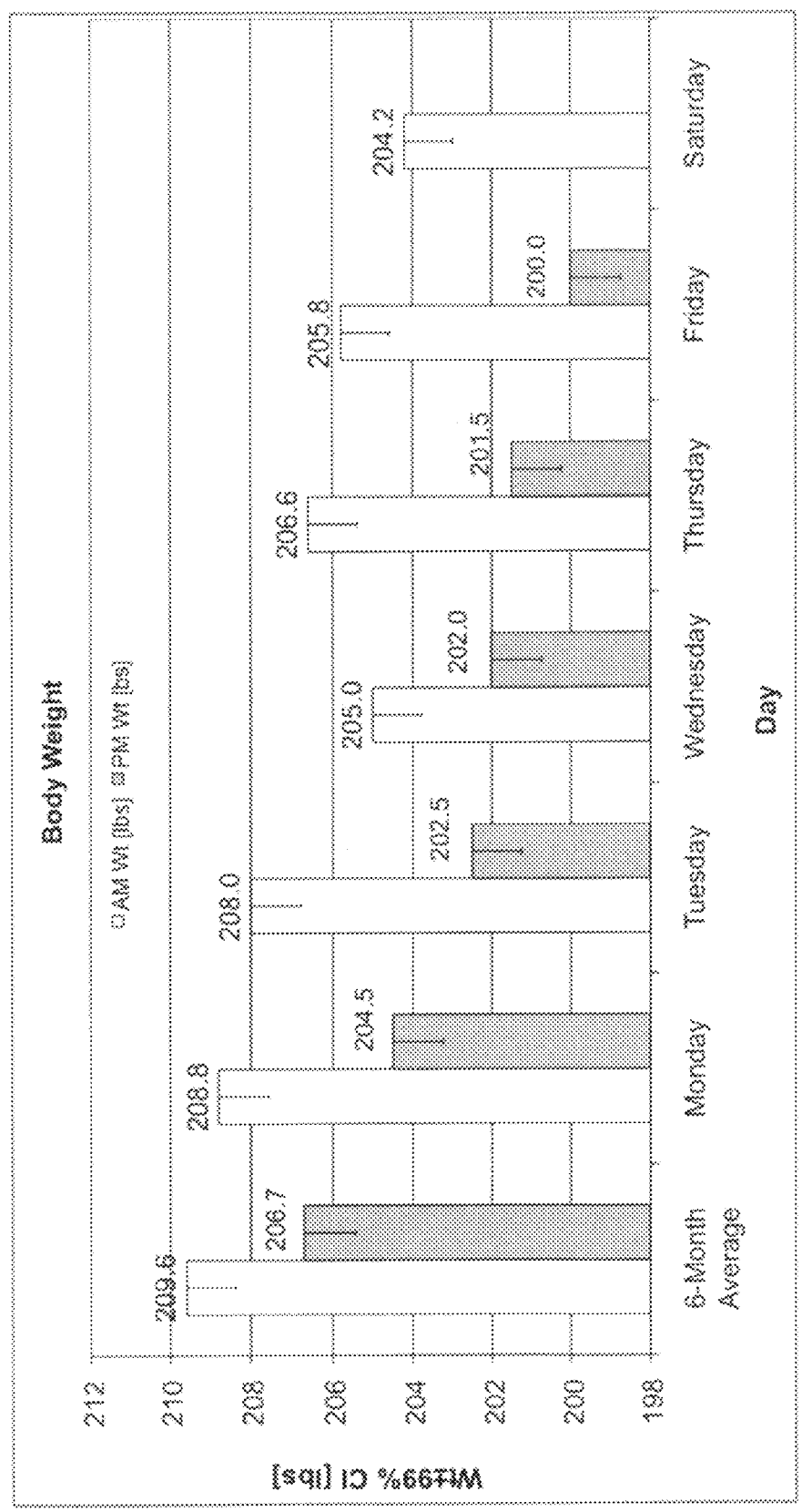
FIG. 12 depicts the change in body weight of a 61-year old male, who had previously exhibited adaptive thermogenesis, during a week following daily dosing of 40 mg NS9/kg-day. Error bars are the 99% confidence interval computed from the previous six-month variation in day-to-day body weight for am and pm weighing.

Results—Although the individual had maintained a stable weight over the previous 12 months, during the week in which his regimen included 40 mg NS9/kg his body weight decreased approximately three percent or six pounds (FIG. 12).

Conclusion—The incorporation of NS9, a supercritical $CO_2$ extract prepared from commercial-scale quantities of powdered *N. sativa* seeds, into the exercise and dietary regimen of an individual experiencing a plateau of weight loss (adaptive thermogenesis) overcame adaptive thermogenesis to facilitate further weight loss.

Example 9

Commercial Supercritical Fluid Extracts of *Nigella sativa* Attenuate LPS/Oxidant-Mediated Loss of Transepithelial Electrical Resistance in Caco-2 Intestinal Epithelial Cells more Effectively than Thymoquinone Objective—The objective of this experiment was to assess the effect of the commercial-scale supercritical $CO_2$ extracts of *N. sativa* produced in Example 1 on the loss of transepithelial electrical resistance in Caco-2 monolayers induced by a cytokine/prooxidant stimulus.

Caco-2 Cells—The protocol for growing and differentiation the human Caco-2 colon andenocarcinoma cells was a modification of Protocol 3 as described by Yamashita et al. [Yamashita, S., Konishi, K., Yamazaki, Y., Taki, Y., Sakane, T., Sezaki, H., and Furuyama, Y. (2002) New and better protocols for a short-term Caco-2 cell culture system, *J Pharm Sci* 91, 669-679]. Caco-2 Human Colon Adenocarcinoma cells were obtained from ATCC (Rockville, Md.; catalog #HTB-37) and maintained in a growth media: DMEM (Dulbecco's Modified Eagles Medium 1×) containing L-glutamine, glucose; Cellgro catalog #35-010CV with the following additions: (1) Penicillin (5,000 IU/mL)/Streptomycin (5,000 μg/mL) Cellgro catalog #30-001C1, (2) 10% FBS—Fetal Bovine Serum, Characterized; Hyclone catalog #SH30071.3, and (3) 1% NEAA—Non Essential Amino Acids; Cellgro catalog #25-025-CI; cells were cultured at 37 C in a humidified air-5% $CO_2$ atmosphere in T175 flasks.

Differentiation of Caco-2 cells to intestinal epithelial cells—BIOCOAT$^R$ HTS Caco-2 Assay System kits (Becton Dickinson, N.J.; catalog #354801) consisting of 24-well fibrillar collagen coated inserts and feeder trays were used in all experiments and plated as follows. Media was removed from the T175 flasks and cells were washed with 10 mLs PBS (phosphate buffered saline 1× without $Ca^{++}$, without $Mg^{++}$; Cellgro #25-053-CI). PBS was removed and 5 mL of Trypsin/ EDTA (1×, 0.25% Trypsin/2.21 mM EDTA in HBSS; Cellgro #25-053-CI) were added to the flask and the flask placed at 37 C until cells were visibly floating, approximately 3-5 minutes. Five mL of growth media were added to the flask to neutralize the trypsin. This solution was then transferred to a sterile 50 mL tube. Eight μL were sampled and placed in a hemocytometer for counting under a microscope. Five-hundred μL of cell solution were placed in the upper chamber of each insert so that the final density per well was at least $6.6 \times 10^5$ cells/$cm^2$. Thirty-five mL of growth media were then added to the feeder tray and plate incubated at 37 C with 5%

$CO_2$ and 100% humidity for 20-24 hours. At this time, media were removed from the inserts by decanting and from the feeder tray by aspiration. Media were then added for the cell differentiation phase; Entero-STIM™ Medium was prepared as per assay kit instructions (Becton Dickinson, N.J.; catalog #354801), 500 µL to the upper chamber of each insert and 35 mL added to the feeder tray.

This medium was refreshed after 48 hours. The following day the plates were prepared for treatment. Media were removed from the upper chamber of the inserts so that the final volume was 300 mL. The insert plate was removed from the feeder tray and placed directly on a 24-well plate. One mL of Entero-STIM™ Medium was added to each well.

Test materials were solubilized or suspended by sonication for 5 minutes in DMSO as a 500× stock and added to top wells in 0.6 µL to achieve the tabulated concentrations. DMSO was added to both negative and positive controls at the same 0.1% concentration as the test wells. Test materials remained on the monolayers for 1 hour, at which time all positive and test cells were treated with 10 uM $H_2O_2$ and 50 µg/mL lipopolysaccharide (LPS, Sigma, St. Louis).

Transepithelial Electrical Resistance Assay—Baseline transepithelial electrical resistance (TEER) measurements of the Caco-2 monolayers were made using a Millicell$^R$-ERS system (Millipore Corporation, Bedford, Mass.). Measurements of TEER were made 1, 2 and 3 hours post treatment.

TABLE 6

Effect of supercritical $CO_2$ extracts of Nigella sativa on LPS/oxidant-mediated decrease of transepithelial electrical resistance in Caco-2 cells

| Treatment | Test Concentration [µg TQ equvalents/mL] | Relative Loss of TEER |
|---|---|---|
| LPS/$H_2O_2$ | — | 100 ± 7.41 |
| Thymoquinone (Sigma) | 5.0 | 111 |
| NS8 | 0.11 | 79.8* |
| NS9 | 0.99 | 117 |
| NS10 | 0.012 | 99.4 |
| NSSpent#1 | 5 µg Spent#1/mL | 99.6 |
| NSSpent#2 | 0.0005 | 85.8* |

**Significantly less than LPS/$H_2O_2$ positive control (p < 0.05)

Data Analysis—After TEER values were normalized to their zero-hour control, the percent change from the positive LPS/$H_2O_2$ control at three hours was tabulated for each fraction. Ninety-five percent confidence intervals (CI) were computed for the positive control, which was set to 100 (Excel, Microsoft, Redmond, Wash.). Values were considered significantly different from the positive control if the mean of the four test wells of the samples fell outside the 95% CI (p<0.05).

Results—TQ, NS9, NS10, and NSSpent#1 had no effect on the LPS/$H_2O_2$-mediated loss of TEER in Caco-2 monolayers (Table 6). NS8 and NSSpent#2, however, reduced the relative LPS/$H_2O_2$-stimulated loss of TEER, respectively, 21 and 14 percent.

Conclusions—Unexpectedly, the degree to which the extracts attenuated LPS/$H_2O_2$ stimulation in differentiated Caco-2 monolayers was out of proportion to the TQ content of all extracts.

Example 10

Supercritical Fluid Extracts of Nigella sativa Attenuate trans-10, cis12-Conjugated Linoleic Acid Isomer Loss of Transepithelial Electrical Resistance in Caco-2 Intestinal Epithelial Cells Background—Several clinical studies have shown that HIV-1 infection is associated with increased permeability of the intestinal tract as evidenced by HIV-induced impairment of mucosal barriers. Exposure to HIV-1 can directly breach the integrity of the mucosal epithelial barrier, and allow translocation of virus and bacteria to impair the gastrointestinal mucosal barrier contributing to further progression of the HIV infection. Additionally, protease inhibitors (PI's) and reverse transcriptase drugs, components of highly active anti-retroviral therapy (HAART) for treating human acquired immunodeficiency syndrome (AIDS), have been limited by undesirable side-effects, such as diarrhea and loss of intestinal membrane integrity (leaky gut syndrome, LGS). Dietary components such as conjugated linoleic acid, suggested for use to overcome hyperlipidemia or lipodystrophy associated with HAART, may also contribute to LGS as the t10-CLA has been shown to negatively affect TEER in Caco-2 cells.

Objective—The objective of this experiment was to assess the effect of the commercial-scale supercritical $CO_2$ extracts of N. sativa produced in Example 1 on the loss of transepithelial electrical resistance in Caco-2 monolayers induced by t10-CLA.

Methods—Experimental methods and data analysis for assessing the loss of TEER in t10-CLA stimulated Caco-2 cells were as described in the previous example with the exception that 50 µM t10-CLA was used to induce TEER loss in place of the LPS/$H_2O_2$ positive control.

TABLE 7

Effect of supercritical $CO_2$ extracts of Nigella sativa on LPS/oxidant-mediated decrease of transepithelial electrical resistance in Caco-2

| Treatment | Test Concentration [µg TQ equvalents/mL] | Relative Loss of TEER |
|---|---|---|
| Solvent Only | — | 0.00* |
| t10-CLA | 50 µM | 100 ± 5.81 |
| Thymoquinone (Sigma) | 5.0 | 44.5* |
| NS8 | 0.11 | 13.9* |
| NS9 | 0.99 | 31.53* |
| NS10 | 0.012 | 25.1* |
| NSSpent#1 | 5 µg Spent#1/mL | 95.8 |
| NSSpent#2 | 0.0005 | 0.00* |

*Significantly less than t10-CLA 50 µM positive control (p < 0.05)

Results—All supercritical $CO_2$ extracts of N. sativa as well as TQ inhibited loss of TEER in t10-CLA-stimulated Caco-2 cells indicating the ability to reduce intestinal monolayer disruption in response to a pro-inflammatory stimulus (Table 7). Spent#1 the extracted powdered seed material had no effect. Unexpectedly, the degree to which the extracts attenuated t10-CLA stimulation in differentiated Caco-2 monolayers was out of proportion to the TQ content of all extracts.

Example 11

Supercritical Fluid Extracts of Nigella sativa Attenuate trans-10, cis12-Conjugated Linoleic Acid Isomer Mediated Inflammation in 3T3-L1 Adipocytes Background—Inflammation plays a role in t10-CLA isomer mediated insulin resistance in adipocytes. One manifestation of this inflammatory response is increased IL-6 and decreased adiponectin secretion by the adipocyte.

Objective—The objective of this experiment was to assess the effect of the commercial-scale supercritical $CO_2$ extracts of *N. sativa* produced in Example 1 on the increase in IL-6 secretion and decreased adiponectin secretion in 3T3-L1 adipocytes induced by the t10-CLA isomer.

The Model—The 3T3-L1 murine fibroblast model as used in Example 4 was used in this experiments.

Test Materials—Commercial-scale supercritical $CO_2$ extracts of *N. sativa* produced in Example 1 were used as test materials. Powdered t10-CLA was provided from Lipid Nutrition (Wormerveer, The Netherlands).

Treatment—Test materials were added four hours prior to the addition of t10-CLA at a concentration of 50 µM. Following overnight incubation, the supernatant media were sampled for determination of IL-6 and adiponectin.

Interleukin-6 assay—The IL-6 secreted into the medium in response to TNFα stimulation was quantified using the Quantikine® Mouse IL-6 Immunoassay kit with no modifications (R&D Systems, Minneapolis, Minn.). Information supplied by the manufacturer indicated that recovery of IL-6 spiked in mouse cell culture media averaged 99% with a 1:2 dilution and the minimum detectable IL-6 concentration ranged from 1.3 to 1.8 pg/mL. All supernatant media samples were diluted 1:30 for quantification.

Adiponectin assay—The adiponectin secreted into the medium was quantified using the Mouse Adiponectin Quantikine® Immunoassay kit with no modifications (R&D Systems, Minneapolis, Minn.). Information supplied by the manufacturer indicated that recovery of adiponectin spiked in mouse cell culture media averaged 103% and the minimum detectable adiponectin concentration ranged from 0.001 to 0.007 ng/ml.

Statistical Calculations and Interpretation—Test materials and were assayed in duplicate, while solvent controls were replicated eight times. IL-6 and adiponectin secretion were represented relative to the IL-6 and adiponectin secretion of the t10-CLA only controls as the IL-6 and adiponectin index and differences among the means were analyzed by the student's t-test assuming a five percent probability of a type I error (Excel; Microsoft, Redmond, Wash.).

Results—Treatment with 50 µM t10-CLA induced a 8-fold increase in IL-6 secretion and 65 percent reduction in adiponectin secretion relative to controls (Table 8). All supercritical $CO_2$ extracts of *N. sativa* as well as TQ inhibited IL-6 secretion in t10-CLA-stimulated adipocytes indicating the ability to reduce secretion of inflammatory cytokines in response to a pro-inflammatory stimulus. Similarly, the extracts and TQ attenuated t10-CLA-stimulated decrease of adiponectin secretion. Spent#1 the extracted seed material had no effect. Surprisingly, the degree to which the extracts affected t10-CLA stimulation in 3T3-L1 adipocytes was out of proportion to the TQ content of all extracts.

TABLE 8

Effect of supercritical $CO_2$ extracts of *Nigella sativa* on t10-CLA-mediated inflammation in 3T3-L1 Adipocytes

| Treatment | Test Concentration [µg TQ equvalents/mL] | IL-6 Index | Adiponectin Index |
|---|---|---|---|
| Solvent Only | — | 12.5 | 222 |
| t10-CLA | 50 µM | 100 ± 11 | 100 ± 14 |
| Thymoquinone (Sigma) | 5.0 | 75* | 128* |
| NS8 | 0.11 | 59* | 132* |
| NS9 | 0.99 | 17* | 188* |
| NS10 | 0.012 | 69* | 166* |
| NSSpent#1 | 5 µg Spent#1/mL | 98 | 109 |
| NSSpent#2 | 0.0005 | 54* | 143* |

*Significantly less than t10-CLA 50 µM positive control ($p < 0.05$)

The attenuation of IL-6 secretion and inhibition of adiponectin secretion of adipocytes as demonstrated in this example underscores the potential of these novel supercritical $CO_2$ extracts of *N. sativa* to overcome the diabetogenic effects of t10-CLA. Such extracts would be useful in combination with CLA mixed isomers containing t10-CLA to increase efficacy for weight loss, metabolic syndrome or type 2 diabetes.

Thus, among the various formulations taught there have been disclosed four novel supercritical $CO_2$ extracts of *N. sativa* resulting from production of commercial scale quantities of powdered seed containing about 0.01 to about 39 (% w/w) TQ and produced under specific conditions of temperature, pressure and time of extraction. Methods for the production of these formulations and uses have been described. It will be readily apparent to those skilled in the art, however, that various changes and modifications of an obvious nature may be made without departing from the spirit of the invention, and all such changes and modifications are considered to fall within the scope of the invention as defined by the appended claims. Such changes and modifications would include, but not be limited to, the incipient ingredients added to affect the capsule, tablet, powder, lotion, food or bar manufacturing process as well as vitamins, flavorings and carriers. Other such changes or modifications would include the use of herbs or other botanical products containing the combinations of the preferred embodiments disclosed above. Many additional modifications and variations of the embodiments described herein may be made without departing from the scope, as is apparent to those skilled in the art. The specific embodiments described herein are offered by way of example only.

The invention claimed is:

1. A method of making four, commercial-scale oil extract compositions from seeds of *Nigella sativa* consisting essentially of:
   a. grinding and sieving the seed of *Nigella sativa* to a fine powder of about 20 to 30 mesh;
   b. extracting commercial-scale quantities of the ground seeds with supercritical $CO_2$ at about 140 bar, at about 50° C. for about 30 minutes and collecting the oil fraction as the first extract composition (C1) obtained;
   c. setting aside C1 and continuing the extraction of the ground *Nigella sativa* seeds at about 140 bar, at about 50° C. for about 120 minutes and collecting the oil fraction as the second extract composition obtained (C2);
   d. setting aside C2 and continuing the extraction of the ground *Nigella sativa* seeds by increasing the pressure to about 300 bar, the temperature to about 60° C. and collecting the oil extract for about an additional 180 minutes as the third extract composition (C3) obtained;
   e. formulating fourth extract composition (C4) by mixing the extracted, spent *N. sativa* powdered seeds with the third extract composition (C3) in a ratio of about 24:1.

2. The method according to claim 1, wherein the resulting oil extract composition C2 has a thymoquinone concentration of about 39%.

3. The method according to claim 1, wherein the resulting oil extract composition C2 has a 2,2-diphenyl-1-picrylhydrazyl free radical quenching activity of about 150μmol Trolox equivalents/g thymoquinone.

* * * * *